United States Patent
Schuler et al.

(10) Patent No.: US 10,045,939 B2
(45) Date of Patent: *Aug. 14, 2018

(54) UNIT DOSES, AEROSOLS, KITS, AND METHODS FOR TREATING HEART CONDITIONS BY PULMONARY ADMINISTRATION

(71) Applicant: InCarda Therapeutics, Inc., San Francisco, CA (US)

(72) Inventors: Carlos A. Schuler, Cupertino, CA (US); Rangachari Narasimhan, Saratoga, CA (US)

(73) Assignee: InCarda Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,252

(22) Filed: Feb. 26, 2015

(65) Prior Publication Data
US 2015/0313842 A1 Nov. 5, 2015

Related U.S. Application Data

(63) Continuation of application No. 13/257,249, filed as application No. PCT/US2010/027740 on Mar. 18, 2010, now Pat. No. 8,974,828.

(60) Provisional application No. 61/210,382, filed on Mar. 18, 2009.

(51) Int. Cl.

| A61P 9/06 | (2006.01) |
|---|---|
| A61P 9/00 | (2006.01) |
| A61K 31/277 | (2006.01) |
| A61K 9/00 | (2006.01) |
| A61K 31/4458 | (2006.01) |
| A61K 31/554 | (2006.01) |
| A61K 31/18 | (2006.01) |
| A61K 31/216 | (2006.01) |
| A61K 31/7076 | (2006.01) |
| A61M 11/00 | (2006.01) |
| A61K 31/445 | (2006.01) |
| A61K 31/55 | (2006.01) |

(52) U.S. Cl.
CPC ............ *A61K 9/0078* (2013.01); *A61K 31/18* (2013.01); *A61K 31/216* (2013.01); *A61K 31/445* (2013.01); *A61K 31/4458* (2013.01); *A61K 31/55* (2013.01); *A61K 31/554* (2013.01); *A61K 31/7076* (2013.01); *A61M 11/00* (2013.01); *Y10S 514/821* (2013.01)

(58) Field of Classification Search
None
See application file for complete search history.

(56) References Cited

U.S. PATENT DOCUMENTS

| 3,991,761 A | 11/1976 | Cocozza |
|---|---|---|
| 4,069,819 A | 1/1978 | Valentini et al. |
| 4,114,615 A | 9/1978 | Wetterlin |
| 4,247,066 A | 1/1981 | Frost et al. |
| 4,338,931 A | 7/1982 | Cavazza |
| 4,846,876 A | 7/1989 | Draber et al. |
| 4,995,385 A | 2/1991 | Valentini et al. |
| 5,458,135 A | 10/1995 | Patton et al. |
| 5,619,985 A | 4/1997 | Ohki et al. |
| 5,785,049 A | 7/1998 | Smith et al. |
| 5,855,913 A | 1/1999 | Hanes et al. |
| 5,874,064 A | 2/1999 | Edwards et al. |
| 5,922,675 A | 7/1999 | Baker et al. |
| 5,976,574 A | 11/1999 | Gordon |
| 5,985,248 A | 11/1999 | Gordon et al. |
| 5,985,309 A | 11/1999 | Edwards et al. |
| 6,001,336 A | 12/1999 | Gordon |
| 6,051,256 A | 4/2000 | Platz et al. |
| 6,077,543 A | 6/2000 | Gordon et al. |
| 6,257,233 B1 | 7/2001 | Burr et al. |
| 6,357,490 B1 | 3/2002 | Johnston et al. |
| 6,358,530 B1 | 3/2002 | Eljamal et al. |
| 6,372,258 B1 | 4/2002 | Platz et al. |

(Continued)

FOREIGN PATENT DOCUMENTS

| JP | 2002529393 A | 9/2002 |
|---|---|---|
| WO | WO 95/24183 A1 | 9/1995 |

(Continued)

OTHER PUBLICATIONS

Dell'Orfano, "Drugs for Conversion of Atrial Fibrillation", Am Fam Physician, 58(2), 471-480, Aug. 1, 1998.*
Barbato, et al. Adrenergic Receptors in Human Atherosclerotic Coronary Arteries. Circulation. 2005, 111:288-294.
Borlak, et al. Metabolism of verapamil in cultures of rat alveolar epithelial cells and pharmacokinetics after administration by intravenous and inhalation routes. Drug Metab Dispos. Aug. 2005;33(8):1108-14. Epub May 10, 2005.
European search report and search opinion dated Jan. 21, 2014 for EP Application No. 10754091.6.
Feldman, et al. Analysis of Coronary Response to Various Doses of Intracoronary Nitroglycerin. Circulation. 1982, 66:321-327.

(Continued)

*Primary Examiner* — Robert T. Crow
*Assistant Examiner* — John P Nguyen
(74) *Attorney, Agent, or Firm* — Wilson, Sonsini, Goodrich & Rosati

(57) ABSTRACT

Methods of treating atrial arrhythmia include administering an effective amount of at least one antiarrhythmic pharmaceutical agent to a patient in need thereof, such that the at least one antiarrhythmic pharmaceutical agent first enters the heart through the pulmonary vein to the left atrium. Other methods of treating atrial arrhythmia include administering by inhalation an effective amount of at least one antiarrhythmic pharmaceutical agent to a patient in need thereof. An amount of the at least one antiarrhythmic pharmaceutical agent may peak in the coronary sinus of the heart at a time ranging from 10 seconds to 30 minutes from initiation of the administering. Unit doses, aerosols, and kits are also contemplated.

31 Claims, 12 Drawing Sheets

(56) References Cited

U.S. PATENT DOCUMENTS

| | | | |
|---|---|---|---|
| 6,503,480 | B1 | 1/2003 | Edwards et al. |
| 6,546,929 | B2 | 4/2003 | Burr et al. |
| 7,473,433 | B2 | 1/2009 | Weikert et al. |
| 8,974,828 | B2 | 3/2015 | Schuler et al. |
| 2002/0017295 | A1 | 2/2002 | Weers |
| 2002/0115655 | A1* | 8/2002 | Mehanna ............ A61K 45/06 514/217.03 |
| 2003/0005924 | A1* | 1/2003 | Rabinowitz ........... A61K 9/007 128/200.14 |
| 2003/0079742 | A1* | 5/2003 | Giroux ................. A61M 11/00 128/200.14 |
| 2004/0011358 | A1 | 1/2004 | Smaldone et al. |
| 2004/0035413 | A1 | 2/2004 | Smaldone et al. |
| 2004/0099269 | A1* | 5/2004 | Hale ..................... A61K 9/007 128/203.16 |
| 2004/0105820 | A1 | 6/2004 | Weers et al. |
| 2004/0156792 | A1 | 8/2004 | Tarara et al. |
| 2004/0167228 | A1* | 8/2004 | Rabinowitz .......... A61K 9/007 514/651 |
| 2005/0009776 | A1* | 1/2005 | Gadgil .............. A61K 31/7076 514/46 |
| 2005/0070552 | A1* | 3/2005 | Fedida .................. A61K 31/40 514/255.06 |
| 2005/0211245 | A1 | 9/2005 | Smaldone et al. |
| 2005/0211253 | A1 | 9/2005 | Smaldone et al. |
| 2005/0235987 | A1 | 10/2005 | Smaldone et al. |
| 2006/0034847 | A1 | 2/2006 | Yun et al. |
| 2006/0034906 | A1* | 2/2006 | Boni .................... A61K 9/0078 424/450 |
| 2006/0052333 | A1* | 3/2006 | Belardinelli ......... A61K 31/137 514/47 |
| 2007/0122352 | A1 | 5/2007 | Kunka et al. |
| 2007/0122353 | A1* | 5/2007 | Hale .................... A61K 9/0004 424/46 |
| 2008/0038363 | A1 | 2/2008 | Zaffaroni et al. |
| 2008/0226736 | A1* | 9/2008 | Caponetti ............ A61K 9/0075 424/489 |
| 2008/0275036 | A1 | 11/2008 | Cross et al. |
| 2010/0086606 | A1* | 4/2010 | Ogawa ................. A61K 9/0014 424/489 |
| 2012/0003318 | A1 | 1/2012 | Schuler et al. |

FOREIGN PATENT DOCUMENTS

| | | |
|---|---|---|
| WO | WO 95/31479 A1 | 11/1995 |
| WO | WO 96/32096 A1 | 10/1996 |
| WO | WO 96/32149 A1 | 10/1996 |
| WO | WO 99/16419 A1 | 4/1999 |
| WO | WO 99/16420 A1 | 4/1999 |
| WO | WO 99/16421 A1 | 4/1999 |
| WO | WO 99/16422 A1 | 4/1999 |
| WO | WO 00/07572 A2 | 2/2000 |
| WO | WO-0027359 A1 | 5/2000 |
| WO | WO 00/72904 A1 | 12/2000 |
| WO | WO 01/85136 A2 | 11/2001 |
| WO | WO 01/85137 A2 | 11/2001 |
| WO | WO 02/083220 A2 | 10/2002 |
| WO | WO 2004/071368 A2 | 8/2004 |
| WO | WO 2007/042467 A1 | 4/2007 |
| WO | WO-2007050347 A1 | 5/2007 |
| WO | WO 2008/036247 A1 | 3/2008 |
| WO | WO 2008/051621 A2 | 5/2008 |
| WO | WO 2008/066745 A1 | 6/2008 |
| WO | WO 2008/072190 A2 | 6/2008 |
| WO | WO-2008134630 A1 | 11/2008 |
| WO | WO 2010/019914 A2 | 2/2010 |
| WO | WO 2010/022259 A1 | 2/2010 |
| WO | WO-2010107964 A1 | 9/2010 |

OTHER PUBLICATIONS

Gaglione, et al. Is There Coronary Vasoconstriction after Intracoronary Beta-adrenergic Blockade in Patients with Coronary Artery Disease. J Am Coll Cardiol. 1987, 10:299-310.

Harrison, et al. Effect of Single Doses of Inhaled Lignocaine on FEV1 and Bronchial Reactivity in Asthma. Respir Med. Dec. 1992, 12:1359-635.

International search report and written opinion dated Jul. 12, 2010 for PCT Application No. PCT/US2010/027740.

Noguchi, et al. Effects of Intracoronary Propranolol on Coronary Blood Flow and Regional Myocardial Function in Dogs. Eur J Pharmacol. 1987, 144(2):201-10.

Notice of allowance dated Jan. 21, 2015 for U.S. Appl. No. 13/257,249.

Office action dated Jan. 3, 2013 for U.S. Appl. No. 13/257,249.

Office action dated Sep. 26, 2013 for U.S. Appl. No. 13/257,249.

Office action dated Jun. 20, 2014 for U.S. Appl. No. 13/257,249.

Rabinowitz, et al. Ultra-fast absorption of amorphous pure drug aerosols via deep lung inhalation. J Pharm Sci. Nov. 2006;95(11):2438-51.

Suttorp, et al. The value of class IC antiarrhythmic drugs for acute conversion of paroxysmal atrial fibrillation or flutter to sinus rhythm. J Am Coll Cardiol. Dec. 1990;16(7):1722-7.

Twiss, et al. Efficacy of Calcium Channel Blockers as Maintenance Therapy for Asthma. British J of Clinical Pharmacology. Nov. 2001.

Zalewski, et al. Myocardial Protection during Transient Coronary Artery Occlusion in Man: Beneficial Effects of Regional Beta-adrenergic Blockade. Circulation. 1986, 73:734-73.

Lopez-Vidriero, M.T. Issues relating to safety and efficacy in nebulizer use. Eur. Respir. Rev., 2000, 10:72, 210-212.

Abarbanell, et al. Prehospital management of rapid atrial fibrillation: recommendations for treatment protocols. Am J Emerg Med. Jan. 2001;19(1):6-9.

European Office Action dated Nov. 16, 2017 for European Patent Application No. EP10754091.6.

\* cited by examiner

UNIT DOSES, AEROSOLS, KITS, AND METHODS FOR TREATING HEART CONDITIONS BY PULMONARY ADMINISTRATION

CROSS REFERENCE TO RELATED APPLICATIONS

This application is a continuation of U.S. patent application Ser. No. 13/257,249, filed on Sep. 16, 2011, which is a national phase filing under 35 U.S.C. § 371 of PCT/US2010/027740 filed under the Patent Cooperation Treaty on Mar. 18, 2010, which claims priority to and benefit of U.S. Provisional Patent Application No. 61/210,382, filed on Mar. 18, 2009, by Carlos A. Schuler and Rangachari Narasimhan, the contents of each being hereby incorporated by reference in their entirety.

BACKGROUND OF THE INVENTION

Field of the Invention

The present invention relates to compositions, unit doses, aerosols, and kits for treating certain heart conditions by pulmonary administration and methods thereof.

Background Art

Cardiac arrhythmia (also dysrhythmia) is a term for any of a large and heterogeneous group of conditions in which there is abnormal electrical activity in the heart. The heart beat may be too fast or too slow, and may be regular or irregular.

Atrial arrhythmia is a field with a high level of unmet clinical need. Many drugs used today have been on the market since the early 1980s and 1990s and are mostly inadequate due to either lack of efficacy or a side-effect profile that is primarily cardiac related, that necessitates extensive monitoring of the patient.

What is needed for fast and safe cardioversion (resolution of arrhythmia) is therapy that:

1. Has little to no risk of acceleration of ventricular rate before cardioversion;
2. Slows atrio-ventricular (AV) conduction so that there is rate control and cardioversion at the same time;
3. Has little to no effect in prolonging the QRS interval and should have a low risk of torsade de pointes; and
4. Has little to no negative inotropic effect; it should have only mild negative chronotropic effect, without the risk of severe bradycardia when the patient reverts to sinus rhythm.

None of the current approved drug products exhibit these characteristics. High oral and intravenous (IV) doses required to compensate for absorption, metabolism, and dilution result in blood high blood concentrations for an extended period of time that cause the dangerous adverse cardiac events like pro-arrhythmias, QT prolongation, and torsade de pointes. FELDMAN et al., "Analysis of Coronary Response to Various Doses of Intracoronary Nitroglycerin," Circulation, 66:321-327 (1982); and BARBATO et al., "Adrenergic Receptors in Human Atherosclerotic Coronary Arteries," Circulation, 111:288-294 (2005). Comorbid conditions also limit use of ideal drugs in some patients, for example the case with intravenous adenosine. GAGLIONE et al., "Is There Coronary Vasoconstriction after Intracoronary Beta-adrenergic Blockade in Patients with Coronary Artery Disease," J Am Coll Cardiol, 10:299-310 (1987). Drugs like verapamil and diltiazem injections are second line of therapy requiring close monitoring of patients. NOGUCHI et al., "Effects of Intracoronary Propranolol on Coronary Blood Flow and Regional Myocardial Function in Dogs," Eur J Pharmacol., 144(2):201-10 (1987); and ZALEWSKI et al., "Myocardial Protection during Transient Coronary Artery Occlusion in Man: Beneficial Effects of Regional Beta-adrenergic Blockade," Circulation, 73:734-73 (1986).

Paroxysmal atrial fibrillation (PAF) is a subset of the overall atrial fibrillation (AF) population and is estimated to be 25-30% of the overall AF population. About 2.5 million patients are affected by AF in the United States. The population of PAF patients is estimated to be 900,000 to 1.5 million worldwide.

Paroxysmal supraventricular tachycardia (PSVT) is an arrhythmia that affects younger and healthy populations who are active (e.g., athletes). About 500,000 to 600,000 patients have PSVT in the United States.

Ablation techniques, e.g., RF ablation, are often used to treat arrhythmias. But ablation is expensive with the cost typically ranging from about $25,000 to $36,000 per procedure. Despite the high expense, ablation may not completely correct the arrhythmia. Often, multiple ablation procedures are required to achieve a satisfactory result.

Oral medications, e.g., pills, tend to require high doses and time for onset of action. The oral dose for heart medications generally tends to be well over 1 mg. High doses increase the likelihood of side effects and drug-drug interactions as these patients typically take multiple medications. The time for onset for oral cardiovascular medications tends to be around 60 minutes. Oral antiarrhythmic medications have been predominantly developed for prevention with treatment being given intravenously.

Intravenous injection usually requires a hospital environment for administering a medicine and typically involves a visit to the emergency room (ER). These overheads result in this therapy being expensive compared to therapies where the patients can self-administer their medicines. Intravenous injection requires a dose that is higher than what is actually needed in the heart to compensate for dilution and metabolism. Drug injected by IV passes through the right side of the heart and then the lungs before reaching the left side of the heart. See FIG. 1. The drug remains in the blood stream at a high concentration bathing all the organs and tissues with this drug in a high concentration, until the drug gets excreted through the kidneys or through other metabolic routes (e.g., hepatic). As a result, IV drugs may cause unwanted side effects. Drugs administered via the IV route are significantly diluted in the venous blood volume and lungs before reaching the cardiac circulation.

Injecting the heart directly is usually a last-resort taken by a cardiologist as a life saving measure in an emergency. The doses of the drugs injected directly into the heart in this manner are usually less than their IV and/or oral doses.

In some cases, an unplanned surgery is necessary to save the patient's life. Of course, unplanned surgeries are expensive and risky to the patient.

Cardiac arrhythmias are associated with disabling symptoms like tightness around the chest, palpitations, feeling tired, and sometimes chest pain.

In view of the above, arrhythmias frequently result in emergency room (ER) visits, where intravenous drugs are administered, sometimes necessitating an extended stay in the hospital and in some cases also leading to unplanned invasive procedures. Pipeline Insights: Antiarrhythmics, Datamonitor (June 2006); and TWISS et al., "Efficacy of Calcium Channel Blockers as Maintenance Therapy for Asthma," British J of Clinical Pharmacology (November 2001).

There remains, however, a need for improved compositions and methods for treating heart conditions. Accordingly, there also remains a need for methods of making these compositions.

SUMMARY OF THE INVENTION

Accordingly, the present invention provides compositions, unit doses, aerosols, kits, and methods for treating certain heart conditions. Other features and advantages of the present invention will be set forth in the description of invention that follows, and in part will be apparent from the description or may be learned by practice of the invention. The invention will be realized and attained by the compositions and methods particularly pointed out in the written description and claims hereof.

A first embodiment of the present invention is directed to a method of treating atrial arrhythmia. The method comprises administering an effective amount of at least one antiarrhythmic pharmaceutical agent to a patient in need thereof, such that the at least one antiarrhythmic pharmaceutical agent first enters the heart through the pulmonary vein to the left atrium.

In another aspect, the present invention is directed to a method of treating atrial arrhythmia, e.g., tachycardia. The method comprises administering by inhalation an effective amount of at least one antiarrhythmic pharmaceutical agent to a patient in need thereof, wherein an amount of the at least one antiarrhythmic pharmaceutical agent peaks in the coronary sinus of the heart at a time ranging from 10 seconds to 30 minutes from initiation of the administering.

In yet another aspect, the present invention is directed to a method of self-diagnosing and treating atrial arrhythmia. The method comprises self-diagnosing atrial arrhythmia by detecting at least one of shortness of breath, heart palpitations, and above normal heart rate. The method also comprises self-administering by inhalation an effective amount of at least one antiarrhythmic pharmaceutical agent within two hours of the self-diagnosing.

In another aspect, the present invention is directed to a method of treating atrial arrhythmia, comprising administering by inhalation an effective amount of at least one antiarrhythmic pharmaceutical agent to a patient in need thereof, wherein an electrophysiologic effect is observed, via electrocardiography, at a time ranging from 10 seconds to 30 minutes from initiation of the administering.

In still another aspect, the present invention is directed to a method of treating atrial arrhythmia, comprising administering by inhalation an effective amount of at least one antiarrhythmic pharmaceutical agent to a patient in need thereof, wherein a cardiac score from a monitor implementing an arrhythmia detection algorithm shows a transition from an arrhythmic state to normal sinus rhythm in the patient at a time ranging from 10 seconds to 30 minutes from initiation of the administering.

In yet another aspect, the present invention is directed to a method of treating atrial arrhythmia, comprising administering by inhalation an effective amount of at least one antiarrhythmic pharmaceutical agent to a patient in need thereof, wherein a short form-36 quality of life score of the patient improves at a time ranging from 10 seconds to 30 minutes from initiation of the administering.

In another aspect, the present invention is directed to a unit dose comprising a unit dose receptacle and a composition within the unit dose receptacle. The composition comprises at least one antiarrhythmic pharmaceutical agent in an amount less than or equal to an amount of the same at least one antiarrhythmic pharmaceutical agent administered intravenously in the arm to achieve a minimum effective amount in the coronary sinus, and a pharmaceutically acceptable excipient.

In still another aspect, the present invention is directed to an aerosol comprising particles having a mass median aerodynamic diameter less than 10 µm. The particles comprise at least one antiarrhythmic pharmaceutical agent in an amount less than or equal to an amount of the same at least one antiarrhythmic pharmaceutical agent administered intravenously in the arm to achieve a minimum effective amount in the coronary sinus, and a pharmaceutically acceptable excipient.

Yet another aspect of the present invention is directed to a kit. The kit comprises a container containing at least one antiarrhythmic pharmaceutical agent and an aerosolization device.

BRIEF DESCRIPTION OF THE DRAWINGS

The present invention is further described in the description of invention that follows, in reference to the noted plurality of non-limiting drawings, wherein.

DESCRIPTION OF THE INVENTION

Figure 1:
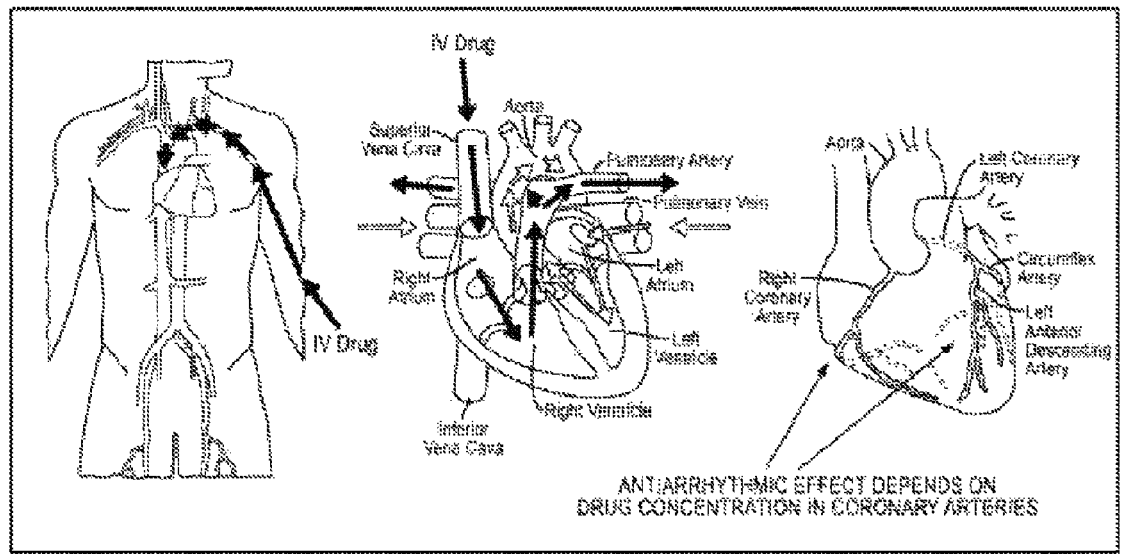
FIG. 1 shows how prior art intravenous drug passes through the heart and lungs before reaching coronary arteries.

It is to be understood that unless otherwise indicated the present invention is not limited to specific formulation components, drug delivery systems, manufacturing techniques, administration steps, or the like, as such may vary. In this regard, unless otherwise stated, a reference to a compound or component includes the compound or component by itself, as well as the compound or component in combination with other compounds or components, such as mixtures of compounds.

Before further discussion, a definition of the following terms will aid in the understanding of the present invention.

As used herein, the singular forms "a," "an," and "the" include plural referents unless the context clearly dictates otherwise. Thus, for example, reference to "an antiarrhythmic pharmaceutical agent" includes not only a single active agent but also a combination or mixture of two or more different active agents.

Reference herein to "one embodiment," "one version," or "one aspect" shall include one or more such embodiments, versions or aspects, unless otherwise clear from the context.

As used herein, the term "solvate" is intended to include, but not be limited to, pharmaceutically acceptable solvates.

As used herein, the term "pharmaceutically acceptable solvate" is intended to mean a solvate that retains one or more of the biological activities and/or properties of the antiarrhythmic pharmaceutical agent and that is not biologically or otherwise undesirable. Examples of pharmaceutically acceptable solvates include, but are not limited to, antiarrhythmic pharmaceutical agents in combination with water, isopropanol, ethanol, methanol, DMSO, ethyl acetate, acetic acid, ethanolamine, or combinations thereof.

As used herein, the term "salt" is intended to include, but not be limited to, pharmaceutically acceptable salts.

As used herein, the term "pharmaceutically acceptable salt" is intended to mean those salts that retain one or more of the biological activities and properties of the free acids and bases and that are not biologically or otherwise undesirable. Illustrative examples of pharmaceutically acceptable salts include, but are not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, di nitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the antiarrhythmic pharmaceutical agent is a base, the desired salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acids such as glucuronic acid and galacturonic acid, alpha-hydroxy acids such as citric acid and tartaric acid, amino acids such as aspartic acid and glutamic acid, aromatic acids such as benzoic acid and cinnamic acid, sulfonic acids such as p-toluenesulfonic acid and ethanesulfonic acid, or the like.

If the antiarrhythmic pharmaceutical agent is an acid, the desired salt may be prepared by any suitable method known in the art, including treatment of the free acid with an inorganic or organic base, such as an amine (primary, secondary or tertiary), an alkali metal or alkaline earth metal hydroxide, or the like. Illustrative examples of suitable salts include organic salts derived from amino acids such as glycine and arginine, ammonia, primary, secondary and tertiary amines, and cyclic amines such as piperidine, morpholine and piperazine, and inorganic salts derived from sodium, calcium, potassium, magnesium, manganese, iron, copper, zinc, aluminum and lithium.

As used herein, "atrial arrhythmia" means an arrhythmia that affects at least one atrium and does not include bradycardia. For instance, atrial arrhythmia may originate in and affect at least one atrium.

As used herein, "tachycardia" means an arrhythmia in which the heart beat is too fast. For instance, tachycardia may involve a resting heart rate of over 100 beats per minute, such as greater than 110, greater than 120, or greater than 130 beats minute.

As used herein, the phrase "heart rhythm arrhythmia" means an arrhythmia in which the heart beat is irregular.

As used herein, the "amount of the at least one antiarrhythmic pharmaceutical agent in blood in the coronary sinus of the heart" may be measured by extracting a sample from the coronary sinus of the heart by using a cannula. The amount of antiarrhythmic pharmaceutical agent in the sample may then be determined by known means, such as bioanalytical techniques that employ analytical equipment such as LC-MS/MS. Thus, the amount of antiarrhythmic pharmaceutical agent in the blood in the heart may be measured for any particular time.

As used herein, the terms "treating" and "treatment" refer to reduction in severity and/or frequency of symptoms, elimination of symptoms and/or underlying cause, reduction in likelihood of the occurrence of symptoms and/or underlying cause, and/or remediation of damage. Thus, "treating" a patient with an active agent as provided herein includes prevention of a particular condition, disease, or disorder in a susceptible individual as well as treatment of a clinically symptomatic individual.

As used herein, "nominal amount" refers to the amount contained within the unit dose receptacle(s) that are administered.

As used herein, "effective amount" refers to an amount covering both therapeutically effective amounts and prophylactically effective amounts.

As used herein, a "therapeutically effective amount" of an active agent refers to an amount that is effective to achieve a desired therapeutic result. A therapeutically effective amount of a given active agent will typically vary with respect to factors such as the type and severity of the disorder or disease being treated and the age, gender, and weight of the patient.

Unless otherwise specified, the term "therapeutically effective amount" includes a "prophylactically effective amount," i.e., an amount of active agent that is effective to prevent the onset or recurrence of a particular condition, disease, or disorder in a susceptible individual.

As used herein, the phrase "minimum effective amount" means the minimum amount necessary to achieve an effective amount.

As used herein, "mass median diameter" or "MMD" refers to the median diameter of a plurality of particles, typically in a polydisperse particle population, i.e., consisting of a range of particle sizes. MMD values as reported herein are determined by laser diffraction (Sympatec Helos, Clausthal-Zellerfeld, Germany), unless the context indicates otherwise. For instance, for powders the samples are added directly to the feeder funnel of the Sympatec RODOS dry powder dispersion unit. This can be achieved manually or by agitating mechanically from the end of a VIBRI vibratory feeder element. Samples are dispersed to primary particles via application of pressurized air (2 to 3 bar), with vacuum depression (suction) maximized for a given dispersion pressure. Dispersed particles are probed with a 632.8 nm laser beam that intersects the dispersed particles' trajectory at right angles. Laser light scattered from the ensemble of particles is imaged onto a concentric array of photomultiplier detector elements using a reverse-Fourier lens assembly. Scattered light is acquired in time-slices of 5 ms. Particle size distributions are back-calculated from the scattered light spatial/intensity distribution using a proprietary algorithm.

As used herein, "geometric diameter" refers to the diameter of a single particle, as determined by microscopy, unless the context indicates otherwise.

As used herein, "mass median aerodynamic diameter" or "MMAD" refers to the median aerodynamic size of a plurality of particles or particles, typically in a polydisperse population. The "aerodynamic diameter" is the diameter of a unit density sphere having the same settling velocity, generally in air, as a powder and is therefore a useful way to characterize an aerosolized powder or other dispersed particle or particle formulation in terms of its settling behavior. The aerodynamic diameter encompasses particle or particle shape, density, and physical size of the particle or particle. As used herein, MMAD refers to the median of the aerodynamic particle or particle size distribution of aerosolized particles determined by cascade impaction, unless the context indicates otherwise.

As used herein, the term "emitted dose" or "ED" refers to an indication of the delivery of particles from an aerosolization device after an actuation or dispersion event from a unit dose receptacle or reservoir. ED is defined as the ratio of the dose delivered by an inhaler device to the nominal dose (i.e., the mass of powder or liquid per unit dose placed into a suitable inhaler device prior to firing). The ED is an experimentally determined amount, and may be determined using an in vitro system that mimics patient dosing. For instance, to determine an ED value for a dry powder, a nominal dose of dry powder is placed into a Turbospin® DPI device (PH&T, Italy), described in U.S. Pat. Nos. 4,069,819 and 4,995,385, which are incorporated herein by reference in their entireties. The Turbospin® DPI is actuated, dispersing the powder. The resulting aerosol cloud is then drawn from the device by vacuum (30 L/min) for 2.5 seconds after actuation, at which point it is captured on a tared glass fiber filter (Gelman, 47 mm diameter) attached to the device mouthpiece. The amount of powder that reaches the filter constitutes the delivered dose. For example, for a capsule containing 5 mg of dry powder, capture of 4 mg of powder on the tared filter would indicate an ED of 80% (=4 mg (delivered dose)/5 mg (nominal dose)).

As used herein, "passive dry powder inhaler" refers to an inhalation device that relies upon a patient's inspiratory effort to disperse and aerosolize a pharmaceutical composition contained within the device in a reservoir or in a unit dose form and does not include inhaler devices which comprise a means for providing energy, such as pressurized gas and vibrating or rotating elements, to disperse and aerosolize the drug composition.

As used herein, "active dry powder inhaler" refers to an inhalation device that does not rely solely on a patient's inspiratory effort to disperse and aerosolize a pharmaceutical composition contained within the device in a reservoir or in a unit dose form and does include inhaler devices that comprise a means for providing energy to disperse and aerosolize the drug composition, such as pressurized gas and vibrating or rotating elements.

By a "pharmaceutically acceptable" component is meant a component that is not biologically or otherwise undesirable, i.e., the component may be incorporated into a pharmaceutical formulation of the invention and administered to a patient as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

As used herein, "P wave" represents the wave of depolarization that spreads from the SA node throughout the atria, and is usually 0.08 to 0.1 seconds (80-100 ms) in duration.

As used herein, "short form-36 quality of life" means the Short Form 36 (SF-36) survey of patient health (updated August 2005). The SF-36 consists of eight scaled scores, which are the sums of the questions in their section. Each scale is directly transformed into a 0-100 scale on the assumption that each question carries equal weight. The eight sections are: (1) vitality; (2) physical functioning; (3) bodily pain; (4) general health perceptions; (5) physical role functioning; (6) emotional role functioning; (7) social role functioning; and (8) mental health.

As used herein, "preservative" means cresols and benzoates. Thus, "substantially preservative-free" means that a composition does not include a substantial amount of any cresols and/or benzoates. For instance, "substantially preservative-free" compositions comprise less than 1 wt %, such as less than 0.5 wt %, less than 0.4 wt %, less than 0.3 wt %, less than 0.2 wt %, or less than 0.1 wt %, of preservative. Of course, "preservative-free" means that no preservative is present.

As used herein, "substantially tasteless" means a composition that has substantially little to no taste upon initial ingestion.

As an overview, the present invention relates to methods of treating atrial arrhythmia. The methods may comprise administering an effective amount of at least one antiarrhythmic pharmaceutical agent to a patient in need thereof, such that the at least one antiarrhythmic pharmaceutical agent first enters the heart through the pulmonary vein to the left atrium.

In one aspect, a method of treating atrial arrhythmia comprises administering by inhalation an effective amount of at least one antiarrhythmic pharmaceutical agent to a patient in need thereof, wherein an amount of the at least one antiarrhythmic pharmaceutical agent peaks in the coronary sinus of the heart at a time ranging from 10 seconds to 30 minutes from initiation of the administering.

In yet another aspect, the present invention is directed to a method of self-diagnosing and treating atrial arrhythmia. The method comprises self-diagnosing atrial arrhythmia by detecting at least one of shortness of breath, heart palpitations, and above normal heart rate. The method also comprises self-administering by inhalation an effective amount of at least one antiarrhythmic pharmaceutical agent within two hours of the self-diagnosing.

In another aspect, a method of treating atrial arrhythmia comprises administering by inhalation an effective amount of at least one antiarrhythmic pharmaceutical agent to a patient in need thereof, wherein an electrophysiologic effect is observed, via electrocardiography, at a time ranging from 10 seconds to 30 minutes from initiation of the administering.

In still another aspect, a method of treating atrial arrhythmia comprises administering by inhalation an effective amount of at least one antiarrhythmic pharmaceutical agent to a patient in need thereof, wherein a cardiac score from a monitor implementing an arrhythmia detection algorithm shows a transition from an arrhythmic state to normal sinus rhythm in the patient at a time ranging from 10 seconds to 30 minutes from initiation of the administering.

In yet another aspect, a method of treating atrial arrhythmia comprises administering by inhalation an effective amount of at least one antiarrhythmic pharmaceutical agent to a patient in need thereof, wherein a short form-36 quality of life score of the patient improves at a time ranging from 10 seconds to 30 minutes from initiation of the administering.

In another aspect, a unit dose comprises a unit dose receptacle and a composition within the unit dose receptacle. The composition comprises at least one antiarrhythmic pharmaceutical agent in an amount less than or equal to an amount of the same at least one antiarrhythmic pharmaceutical agent administered intravenously in the arm to achieve a minimum effective amount in the coronary sinus, and a pharmaceutically acceptable excipient.

In still another aspect, an aerosol comprises particles having a mass median aerodynamic diameter less than 10 µm. The particles comprise at least one antiarrhythmic pharmaceutical agent in an amount less than or equal to an amount of the same at least one antiarrhythmic pharmaceutical agent administered intravenously in the arm to achieve a minimum effective amount in the coronary sinus, and a pharmaceutically acceptable excipient.

In yet another aspect, a kit comprises a container containing at least one antiarrhythmic pharmaceutical agent and an aerosolization device.

In certain embodiments, the present invention includes "pharmaco-rescue-therapies" to provide fast cardioversion in patients with atrial arrhythmias like Paroxysmal Ventricular Tachycardia (PSVT), and Paroxysmal Atrial Fibrillation (PAF). The pharmaco-rescue-therapies are usually intended for self-administration of the medicine by inhalation.

Figure 2A:
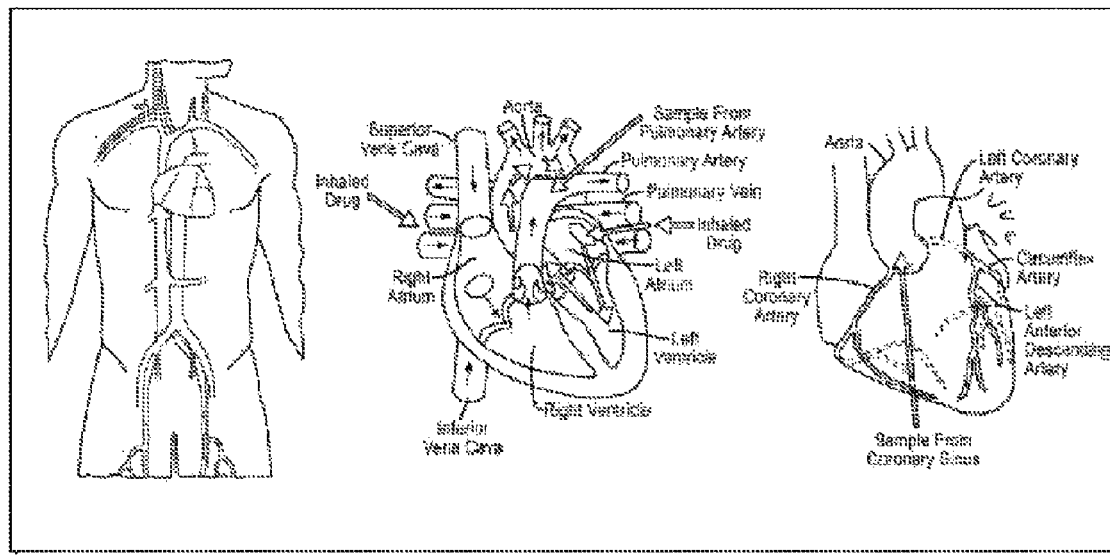
FIG. 2A shows how inhaled drug of the present invention passes through directly from the lungs to coronary arteries.
Figure 2B:
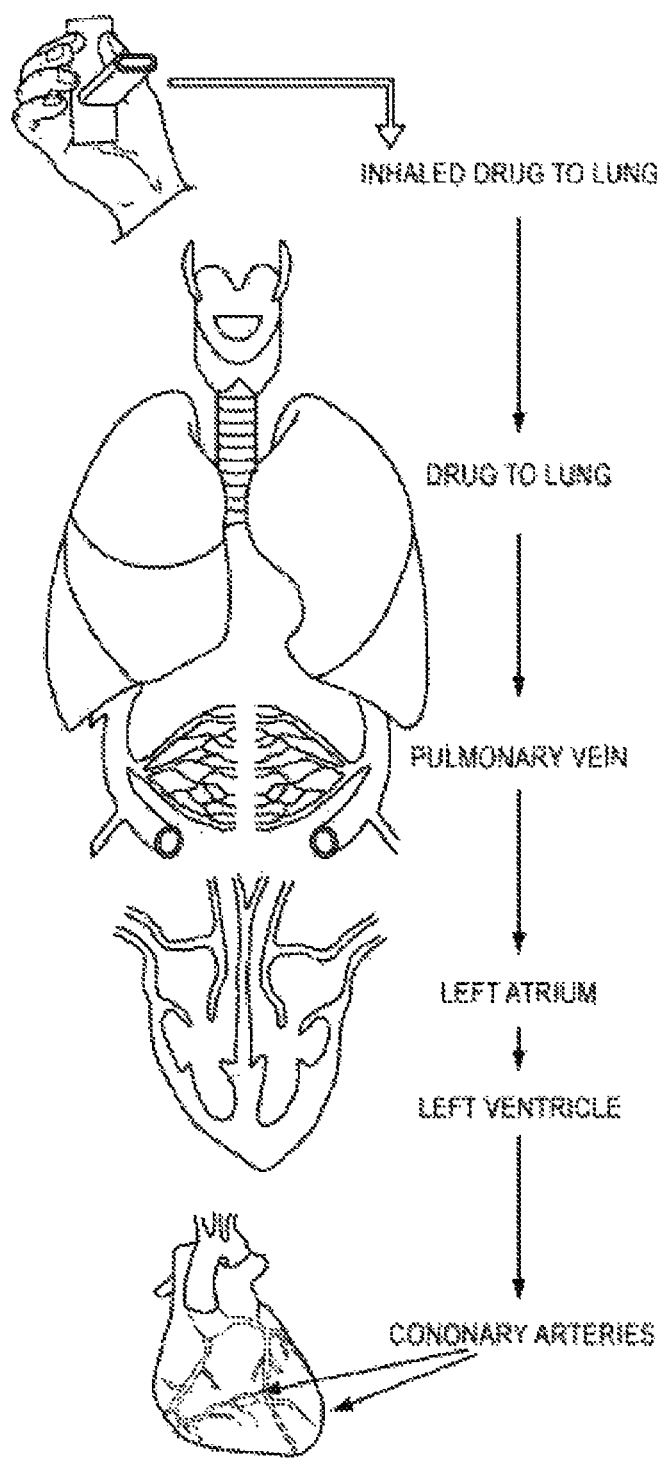
FIG. 2B shows how inhaled drug of the present invention passes through the pulmonary vein to the left atrium.

Inhalation is the shortest route for a drug to reach the heart, next only to intracardial injection, as shown in FIGS. 2A and 2B. Drugs delivered by inhalation generally exhibit "pulsatile pharmacokinetics" of transient high drug concentrations, followed by dilution to sub-therapeutic levels. This characteristic is expected to reduce much of the dose dependent pro-arrhythmia and QT prolongation seen with both oral and IV therapies. See FELDMAN et al., "Analysis of Coronary Response to Various Doses of Intracoronary Nitroglycerin," Circulation, 66:321-327 (1982); and BARBATO et al., "Adrenergic Receptors in Human Atherosclerotic Coronary Arteries," Circulation, 111:288-294 (2005).

Thus, in some embodiments, the present invention involves a rapid acting inhaled product with a fast onset of action compared to oral medicine. The product is expected to be at least as fast as intravenous medicine. In some embodiments, an amount of the at least one antiarrhythmic pharmaceutical agent peaks in the coronary sinus of the heart at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In certain embodiments, an electrophysiologic effect is observed, via electrocardiography, at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In some embodiments, a cardiac score from a monitor implementing an arrhythmia detection algorithm shows a transition from an arrhythmic state to normal sinus rhythm in the patient at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In some embodiments, a short form-36 quality of life score of the patient improves at a time ranging from 10 seconds to 30 minutes, such as 30 seconds to 20 minutes, 1 minute to 10 minutes, 2 minutes to 8 minutes, or 2.5 minutes to 5 minutes, from initiation of the administering. In certain embodiments, the patient has normal sinus rhythm within 30 minutes, such as within 10 minutes, of initiating the administering.

In some aspects, the present invention involves low doses that are safe and effective. Other aspects typically involve low premature metabolism and low drug-drug interaction.

The present invention includes non-invasive drug delivery to the heart. The lung is shortest route for drug to heart with minimal dilution next to intra-cardial injection. Drugs delivered via the lung have a fast onset action compared to those delivered via the oral route. Pipeline Insights: Antiarrhythmics, Datamonitor (June 2006). Pulmonary drug delivery to the heart is at least equivalent to a portable intravenous injection. Inhaled drugs (e.g., verapamil, diltiazem, lidocaine, ibutilide, procainamide, and propafenone) are expected to exhibit "pulsatile pharmacokinetics" of transient high drug concentrations, followed by dilution to sub-therapeutic levels.

Existing cardiovascular drugs tend to be small molecules with high lipid solubility. These lipid soluble molecules (e.g., diltiazem, verapamil, ibutilide, propafenone) are expected to have a high pulmonary bioavailability and fast rate of pulmonary absorption. This ensures that they reach the heart through the pulmonary veins.

The pulsatile pharmacokinetic behavior of the drugs show that the drug is diluted within a few seconds of reaching effective concentrations in the heart and is diluted to subtherapeutic levels in the volume of the blood. This characteristic will minimize drug-drug interactions that produce significant toxicological responses normally seen at steady state.

Thus, in certain embodiments, the present invention relates to achieving transient high drug concentrations in the heart that effect rate and rhythm changes in the heart within a short period of time allowing for treatment of episodic arrhythmias such as paroxysmal atrial arrhythmias.

Figure 3:
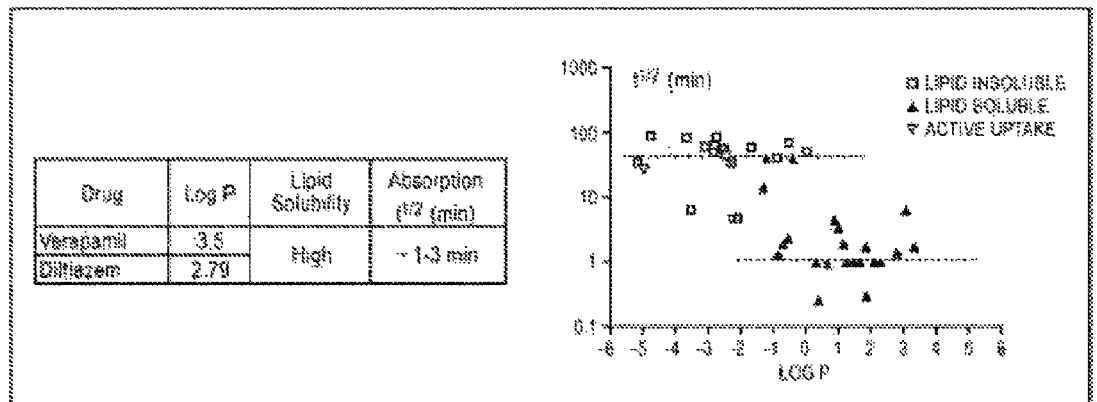
FIG. 3 shows that molecules with high Log-P values and those that have high lipid solubility are likely to exhibit faster absorption through the lung.
Figure 4:
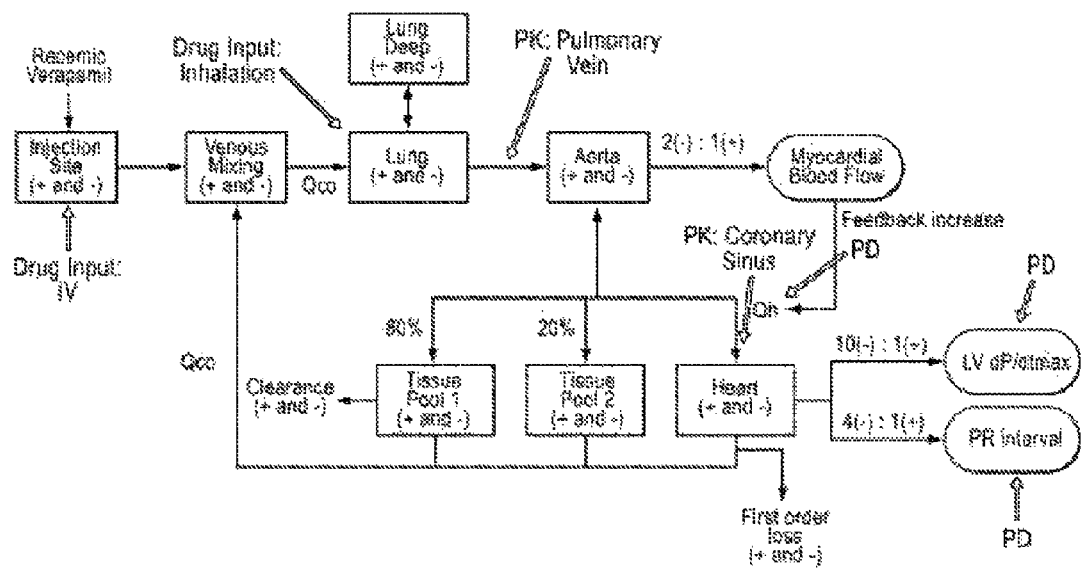
FIG. 4 shows a six compartment PK-PD model to compare intravenous and pulmonary delivery.
Figure 5:
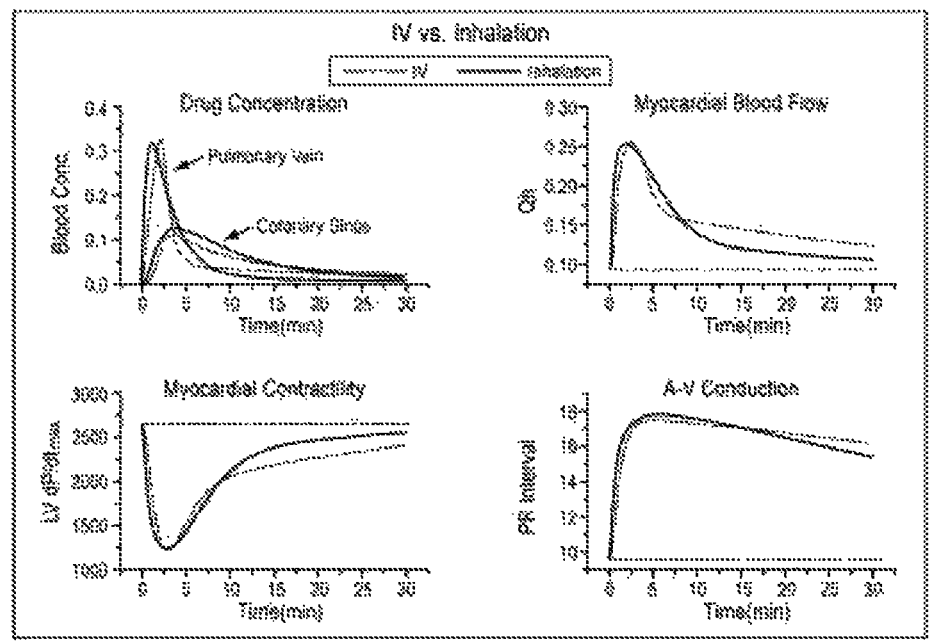
FIG. 5 shows the results of a simulation comparing intravenous and pulmonary delivery of verapamil.
Figure 6:
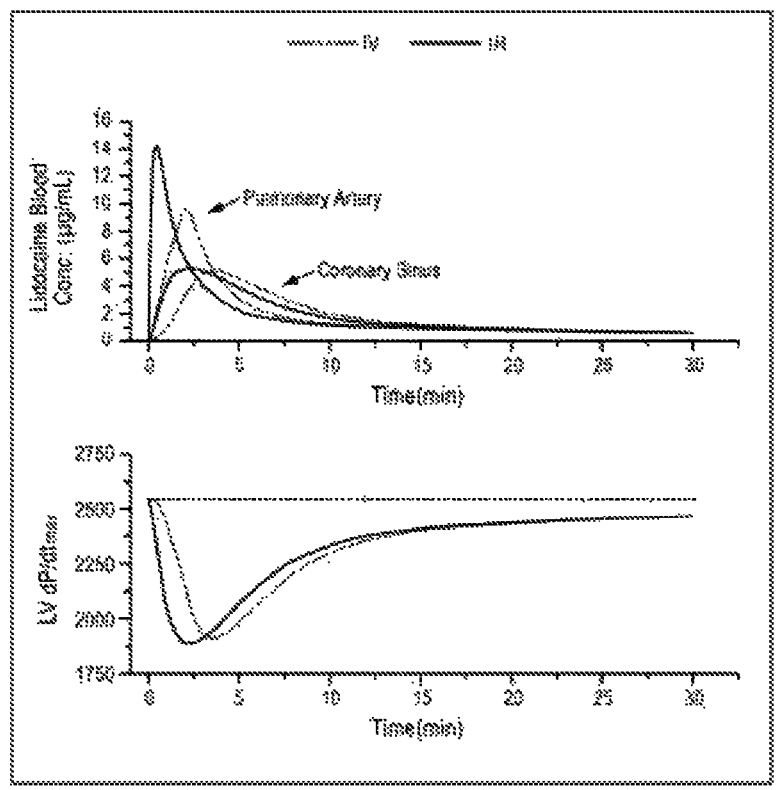
FIG. 6 shows the results of a simulation comparing intravenous and pulmonary delivery of lidocaine.

The results of the invention are surprising and unexpected. In this regard, the antiarrhythmic pharmaceutical agents pass through the lungs quickly. For instance, verapamil and diltiazem will ionize if in salt form, so the base will pass through the lungs quickly. In some aspects, the methods of the present invention take advantage of fast onset of action, high drug bioavailability, and fast absorption through the lung. Most cardiovascular drugs are small molecules that have high lipid solubility and are therefore expected to have high pulmonary bioavailability and a fast rate of absorption. FIG. 3 shows the log-p values and lipid solubility of exemplary cardiovascular molecules along with their expected high pulmonary bioavailability.

Another reason why the results of the present invention are surprising and unexpected involves the rate at which the antiarrhythmic pharmaceutical agents pass through the heart. While a skilled artisan might expect the rate to be too fast, modeling indicates that the drug will not pass through the heart too fast. Thus, a therapeutic effect is achieved despite fast pass-through and despite only one pass-through at therapeutic levels.

In view of the above, in one or more embodiments of the invention, a composition comprises an antiarrhythmic pharmaceutical agent. Examples of antiarrhythmic pharmaceutical agents include, but are not limited to, class Ia (sodium channel blockers, intermediate association/dissociation), class Ib (sodium channel blockers, fast association/dissociation), class Ic (sodium channel blocker, slow association/dissociation), class II (beta blockers), class III (potassium channel blockers), class IV (calcium channel blockers), and class V (unknown mechanisms) antiarrhythmics.

Class Ia antiarrhythmics include, but are not limited to, quinidine, procainamide, and disopyramide. Class Ib antiarrhythmics include, but are not limited to, lidocaine, tocainide, phenytoin, moricizine, and mexiletine. Class Ic antiarrhythmics include, but are not limited to, flecainide, propafenone, and moricizine. Class H antiarrhythmics include, but are not limited to, propranolol, acebutolol, soltalol, esmolol, timolol, metoprolol, and atenolol. Class III antiarrhythmics include, but are not limited to, amiodarone, sotalol, bretylium, ibutilide, E-4031 (methanesulfonamide), vernakalant, and dofetilide. Class IV antiarrhythmics include, but are not limited to, bepridil, nitrendipine, amlodipine, isradipine, nifedipine, nicardipine, verapamil, and diltiazem. Class V antiarrhythmics include, but are not limited to, digoxin and adenosine.

The present invention also includes derivatives of the above antiarrhythmic pharmaceutical agents such as solvates, salts, solvated salts, esters, amides, hydrazides, N-alkyls, and/or N-amino acyls. Examples of ester derivatives include, but are not limited to, methyl esters, choline esters, and dimethylaminopropyl esters. Examples of amide derivatives include, but are not limited to, primary, secondary, and tertiary amides. Examples of hydrazide derivatives include, but are not limited to, N-methylpiperazine hydrazides. Examples of N-alkyl derivatives include, but are not limited to, N',N',N'-trimethyl and N',N'-dimethylaminopropyl succininimidyl derivatives of antiarrhythmic pharmaceutical agent methyl esters. Examples of N-aminoacyl derivatives include, but are not limited to, N-ornithyl-, N-diaminopropionyl-, N-lysil-, N-hexamethyllysil-, and N-piperdine-propionyl- or N',N'-methyl-1-piperazine-propionyl-antiarrhythmic pharmaceutical agent methyl esters.

The antiarrhythmic pharmaceutical agents may exist as single stereoisomers, racemates, and/or mixtures of enantiomers, and/or diastereomers. All such single stereoisomers, racemates, and mixtures thereof are intended to be within the scope of the present invention. These various forms of the compounds may be isolated/prepared by methods known in the art.

The antiarrhythmic pharmaceutical agents of the present invention may be prepared in a racemic mixture (i.e., mixture of isomers) that contains more than 50%, preferably at least 75%, and more preferably at least 90% of the desired isomer (i.e., 80% enantiomeric or diastereomeric excess). According to particularly preferred embodiments, the compounds of the present invention are prepared in a form that contains at least 95% (90% e.e. or d.e.), even more preferably at least 97.5% (95% e.e. or d.e.), and most preferably at least 99% (98% e.e. or d.e.) of the desired isomer. Compounds identified herein as single stereoisomers are meant to describe compounds used in a form that contains more than 50% of a single isomer. By using known techniques, these compounds may be isolated in any of such forms by slightly varying the method of purification and/or isolation from the solvents used in the synthetic preparation of such compounds.

The pharmaceutical composition according to one or more embodiments of the invention may comprise one or more antiarrhythmic pharmaceutical agents and, optionally, one or more other active ingredients and, optionally, one or more pharmaceutically acceptable excipients. For example, the pharmaceutical composition may comprise neat particles of antiarrhythmic pharmaceutical agent, may comprise neat particles of antiarrhythmic pharmaceutical agent together with other particles, and/or may comprise particles comprising antiarrhythmic pharmaceutical agent and one or more active ingredients and/or one or more pharmaceutically acceptable excipients.

Thus, the pharmaceutical composition according to one or more embodiments of the invention may, if desired, contain a combination of antiarrhythmic pharmaceutical agent and one or more additional active agents. Examples of additional active agents include, but are not limited to, agents that may be delivered through the lungs.

Additional active agents may comprise, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxidants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The additional active agent, when administered by inhalation, may act locally or systemically.

The additional active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of additional active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., monoacylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFFR) gene, deoxyribonuclease (DNase), bactericidal/permeability increasing protein (BPI), anti-CMV antibody, 13-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Additional active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

When a combination of active agents is used, the agents may be provided in combination in a single species of pharmaceutical composition or individually in separate species of pharmaceutical compositions.

The amount of antiarrhythmic pharmaceutical agent in the pharmaceutical composition may vary. The amount of antiarrhythmic pharmaceutical agent(s) is typically at least about 5 wt %, such as at least about 10 wt %, at least about 20 wt %, at least about 30 wt %, at least about 40 wt %, at least about 50 wt %, at least about 60 wt %, at least about 70 wt %, or at least about 80 wt %, of the total amount of the pharmaceutical composition. The amount of antiarrhythmic pharmaceutical agent(s) generally varies between about 0.1 wt % to 100 wt %, such as about 5 wt % to about 95 wt %, about 10 wt % to about 90 wt %, about 30 wt % to about 80 wt %, about 40 wt % to about 70 wt %, or about 50 wt % to about 60 wt %.

As noted above, the pharmaceutical composition may include one or more pharmaceutically acceptable excipient. Examples of pharmaceutically acceptable excipients include, but are not limited to, lipids, metal ions, surfactants, amino acids, carbohydrates, buffers, salts, polymers, and the like, and combinations thereof.

Examples of lipids include, but are not limited to, phospholipids, glycolipids, ganglioside GM1, sphingomyelin, phosphatidic acid, cardiolipin; lipids bearing polymer chains such as polyethylene glycol, chitin, hyaluronic acid, or polyvinylpyrrolidone; lipids bearing sulfonated mono-, di-, and polysaccharides; fatty acids such as palmitic acid, stearic acid, and oleic acid; cholesterol, cholesterol esters, and cholesterol hemisuccinate.

In one or more embodiments, the phospholipid comprises a saturated phospholipid, such as one or more phosphatidylcholines. Exemplary acyl chain lengths are 16:0 and 18:0 (i.e., palmitoyl and stearoyl). The phospholipid content may be determined by the active agent activity, the mode of delivery, and other factors.

Phospholipids from both natural and synthetic sources may be used in varying amounts. When phospholipids are present, the amount is typically sufficient to coat the active agent(s) with at least a single molecular layer of phospholipid. In general, the phospholipid content ranges from about 5 wt % to about 99.9 wt %, such as about 20 wt % to about 80 wt %.

Generally, compatible phospholipids comprise those that have a gel to liquid crystal phase transition greater than about 40° C., such as greater than about 60° C., or greater than about 80° C. The incorporated phospholipids may be relatively long chain (e.g., $C_{16}$-$C_{22}$) saturated lipids. Exemplary phospholipids useful in the present invention include, but are not limited to, phosphoglycerides such as dipalmitoylphosphatidylcholine, distearoylphosphatidylcholine, diarachidoylphosphatidylcholine, dibehenoylphosphatidylcholine, diphosphatidyl glycerols, short-chain phosphatidylcholines, hydrogenated phosphatidylcholine, E-100-3 (available from Lipoid KG, Ludwigshafen, Germany), long-chain saturated phosphatidylethanolamines, long-chain saturated phosphatidylserines, long-chain saturated phosphatidylglycerols, long-chain saturated phosphatidylinositols, phosphatidic acid, phosphatidylinositol, and sphingomyelin.

Examples of metal ions include, but are not limited to, divalent cations, including calcium, magnesium, zinc, iron, and the like. For instance, when phospholipids are used, the pharmaceutical composition may also comprise a polyvalent cation, as disclosed in WO 01/85136 and WO 01/85137, which are incorporated herein by reference in their entireties. The polyvalent cation may be present in an amount effective to increase the melting temperature ($T_m$) of the phospholipid such that the pharmaceutical composition exhibits a $T_m$ which is greater than its storage temperature ($T_m$) by at least about 20° C., such as at least about 40° C. The molar ratio of polyvalent cation to phospholipid may be at least about 0.05:1, such as about 0.05:1 to about 2.0:1 or about 0.25:1 to about 1.0:1. An example of the molar ratio of polyvalent cation:phospholipid is about 0.50:1. When the polyvalent cation is calcium, it may be in the form of calcium chloride. Although metal ion, such as calcium, is often included with phospholipid, none is required.

As noted above, the pharmaceutical composition may include one or more surfactants. For instance, one or more surfactants may be in the liquid phase with one or more being associated with solid particles or particles of the composition. By "associated with" it is meant that the pharmaceutical compositions may incorporate, adsorb, absorb, be coated with, or be formed by the surfactant. Surfactants include, but are not limited to, fluorinated and nonfluorinated compounds, such as saturated and unsaturated lipids, nonionic detergents, nonionic block copolymers, ionic surfactants, and combinations thereof. It should be emphasized that, in addition to the aforementioned surfactants, suitable fluorinated surfactants are compatible with the teachings herein and may be used to provide the desired preparations.

Examples of nonionic detergents include, but are not limited to, sorbitan esters including sorbitan trioleate (Span™ 85), sorbitan sesquioleate, sorbitan monooleate, sorbitan monolaurate, polyoxyethylene (20) sorbitan monolaurate, and polyoxyethylene (20) sorbitan monooleate, oleyl polyoxyethylene (2) ether, stearyl polyoxyethylene (2) ether, lauryl polyoxyethylene (4) ether, glycerol esters, and sucrose esters. Other suitable nonionic detergents can be easily identified using McCutcheon's Emulsifiers and Detergents (McPublishing Co., Glen Rock, N.J.), which is incorporated herein by reference in its entirety.

Examples of block copolymers include, but are not limited to, diblock and triblock copolymers of polyoxyethylene and polyoxypropylene, including poloxamer 188 (Pluronic™ F-68), poloxamer 407 (Pluronic™ F-127), and poloxamer 338.

Examples of ionic surfactants include, but are not limited to, sodium sulfosuccinate, and fatty acid soaps.

Examples of amino acids include, but are not limited to hydrophobic amino acids. Use of amino acids as pharmaceutically acceptable excipients is known in the art as disclosed in WO 95/31479, WO 96/32096, and WO 96/32149, which are incorporated herein by reference in their entireties.

Examples of carbohydrates include, but are not limited to, monosaccharides, disaccharides, and polysaccharides. For example, monosaccharides such as dextrose (anhydrous and monohydrate), galactose, mannitol, D-mannose, sorbitol, sorbose and the like; disaccharides such as lactose, maltose, sucrose, trehalose, and the like; trisaccharides such as raffinose and the like; and other carbohydrates such as starches (hydroxyethylstarch), cyclodextrins, and maltodextrins.

Examples of buffers include, but are not limited to, tris or citrate.

Examples of acids include, but are not limited to, carboxylic acids.

Examples of salts include, but are not limited to, sodium chloride, salts of carboxylic acids, (e.g., sodium citrate, sodium ascorbate, magnesium gluconate, sodium gluconate, tromethamine hydrochloride, etc.), ammonium carbonate, ammonium acetate, ammonium chloride, and the like.

Examples of organic solids include, but are not limited to, camphor, and the like.

The pharmaceutical composition of one or more embodiments of the present invention may also include a biocompatible, such as biodegradable polymer, copolymer, or blend or other combination thereof. In this respect useful polymers comprise polylactides, polylactide-glycolides, cyclodextrins, polyacrylates, methylcellulose, carboxymethylcellulose, polyvinyl alcohols, polyanhydrides, polylactams, polyvinyl pyrrolidones, polysaccharides (dextrans, starches, chitin, chitosan, etc.), hyaluronic acid, proteins, (albumin, collagen, gelatin, etc.). Those skilled in the art will appreciate that, by selecting the appropriate polymers, the delivery efficiency of the composition and/or the stability of the dispersions may be tailored to optimize the effectiveness of the antiarrhythmic pharmaceutical agent(s).

For solutions, the compositions may include one or more osmolality adjuster, such as sodium chloride. For instance, sodium chloride may be added to solutions to adjust the osmolality of the solution. In one or more embodiments, an aqueous composition consists essentially of the antiarrhythmic pharmaceutical agent, the osmolality adjuster, and water.

Solutions may also comprise a buffer or a pH adjusting agent, typically a salt prepared from an organic acid or base. Representative buffers comprise organic acid salts of citric acid, lactic acid, ascorbic acid, gluconic acid, carbonic acid, tartaric acid, succinic acid, acetic acid, or phthalic acid, Tris, tromethamine hydrochloride, or phosphate buffers. Thus, the buffers include citrates, phosphates, phthalates, and lactates.

Besides the above mentioned pharmaceutically acceptable excipients, it may be desirable to add other pharmaceutically acceptable excipients to the pharmaceutical composition to improve particle rigidity, production yield, emitted dose and deposition, shelf-life, and patient acceptance. Such optional pharmaceutically acceptable excipients include, but are not limited to: coloring agents, taste masking agents, buffers, hygroscopic agents, antioxidants, and chemical stabilizers. Further, various pharmaceutically acceptable excipients may be used to provide structure and form to the particle compositions (e.g., latex particles). In this regard, it will be appreciated that the rigidifying components can be removed using a post-production technique such as selective solvent extraction.

The pharmaceutical compositions of one or more embodiments of the present invention often lack taste. In this regard, although taste masking agents are optionally included within the composition, the compositions often do not include a taste masking agent and lack taste even without a taste masking agent.

The pharmaceutical compositions may also include mixtures of pharmaceutically acceptable excipients. For instance, mixtures of carbohydrates and amino acids are within the scope of the present invention.

The compositions of one or more embodiments of the present invention may take various forms, such as solutions, dry powders, reconstituted powders, suspensions, or dispersions comprising a non-aqueous phase, such as propellants (e.g., chlorofluorocarbon, hydrofluoroalkane).

The solutions of the present invention are typically clear. In this regard, many of the antiarrhythmic pharmaceutical agents of the present invention are water soluble.

In some embodiments, the isotonicity of the solution ranges from isotonic to physiologic isotonicity. Physiologic isotonicity is the isotonicity of physiological fluids.

The compositions typically have a pH ranging from 3.5 to 8.0, such as from 4.0 to 7.5, or 4.5 to 7.0, or 5.0 to 6.5.

For dry powders, the moisture content is typically less than about 15 wt %, such as less than about 10 wt %, less than about 5 wt %, less than about 2 wt %, less than about 1 wt %, or less than about 0.5 wt %. Such powders are described in WO 95/24183, WO 96/32149, WO 99/16419, WO 99/16420, and WO 99/16422, which are incorporated herein by reference in their entireties.

In one version, the pharmaceutical composition comprises antiarrhythmic pharmaceutical agent incorporated into a phospholipid matrix. The pharmaceutical composition may comprise phospholipid matrices that incorporate the active agent and that are in the form of particles that are hollow and/or porous microstructures, as described in the aforementioned WO 99/16419, WO 99/16420, WO 99/16422, WO 01/85136, and WO 01/85137, which are incorporated herein by reference in their entireties. The hollow and/or porous microstructures are useful in delivering the antiarrhythmic pharmaceutical agent to the lungs because the density, size, and aerodynamic qualities of the hollow and/or porous microstructures facilitate transport into the deep lungs during a user's inhalation. In addition, the phospholipid-based hollow and/or porous microstructures reduce the attraction forces between particles, making the pharmaceutical composition easier to deagglomerate during aerosolization and improving the flow properties of the pharmaceutical composition making it easier to process.

In one version, the pharmaceutical composition is composed of hollow and/or porous microstructures having a bulk density less than about 1.0 g/cm$^3$, less than about 0.5 g/cm$^3$, less than about 0.3 g/cm$^3$, less than about 0.2 g/cm$^3$, or less than about 0.1 g/cm$^3$. By providing low bulk density particles or particles, the minimum powder mass that can be filled into a unit dose container is reduced, which eliminates the need for carrier particles. That is, the relatively low density of the powders of one or more embodiments of the present invention provides for the reproducible administration of relatively low dose pharmaceutical compounds. Moreover, the elimination of carrier particles will potentially reduce throat deposition and any "gag" effect or coughing, since large carrier particles, e.g., lactose particles, will impact the throat and upper airways due to their size.

In some aspects, the present invention involves high rugosity particles. For instance, the particles may have a rugosity of greater than 2, such as greater than 3, or greater than 4, and the rugosity may range from 2 to 15, such as 3 to 10.

In one version, the pharmaceutical composition is in dry powder form and is contained within a unit dose receptacle which may be inserted into or near the aerosolization apparatus to aerosolize the unit dose of the pharmaceutical composition. This version is useful in that the dry powder form may be stably stored in its unit dose receptacle for a long period of time. In some examples, pharmaceutical compositions of one or more embodiments of the present invention may be stable for at least 2 years. In some versions, no refrigeration is required to obtain stability. In other versions, reduced temperatures, e.g., at 2-8° C., may be used to prolong stable storage. In many versions, the storage stability allows aerosolization with an external power source.

It will be appreciated that the pharmaceutical compositions disclosed herein may comprise a structural matrix that exhibits, defines or comprises voids, pores, defects, hollows, spaces, interstitial spaces, apertures, perforations or holes. The absolute shape (as opposed to the morphology) of the perforated microstructure is generally not critical and any overall configuration that provides the desired characteristics is contemplated as being within the scope of the invention. Accordingly, some embodiments comprise approximately spherical shapes. However, collapsed, deformed or fractured particles are also compatible.

In one version, the antiarrhythmic pharmaceutical agent is incorporated in a matrix that forms a discrete particle, and the pharmaceutical composition comprises a plurality of the discrete particles. The discrete particles may be sized so that they are effectively administered and/or so that they are available where needed. For example, for an aerosolizable pharmaceutical composition, the particles are of a size that allows the particles to be aerosolized and delivered to a user's respiratory tract during the user's inhalation.

The matrix material may comprise a hydrophobic or a partially hydrophobic material. For example, the matrix material may comprise a lipid, such as a phospholipid, and/or a hydrophobic amino acid, such as leucine or trileucine. Examples of phospholipid matrices are described in WO 99/16419, WO 99/16420, WO 99/16422, WO 01/85136, and WO 01/85137 and in U.S. Pat. Nos. 5,874,064; 5,855,913; 5,985,309; 6,503,480; and 7,473,433, and in U.S. Published App. No. 20040156792, all of which are incorporated herein by reference in their entireties. Examples of hydrophobic amino acid matrices are described in U.S. Pat. Nos. 6,372,258; 6,358,530; and 7,473,433, which are incorporated herein by reference in their entireties.

When phospholipids are utilized as the matrix material, the pharmaceutical composition may also comprise a polyvalent cation, as disclosed in WO 01/85136 and WO 01/85137, which are incorporated herein by reference in their entireties.

According to another embodiment, release kinetics of the composition containing antiarrhythmic pharmaceutical agent(s) is controlled. According to one or more embodiments, the compositions of the present invention provide immediate release of the antiarrhythmic pharmaceutical agent(s). Alternatively, the compositions of other embodiments of the present invention may be provided as non-homogeneous mixtures of active agent incorporated into a matrix material and unincorporated active agent in order to provide desirable release rates of antiarrhythmic pharmaceutical agent According to this embodiment, antiarrhythmic pharmaceutical agents formulated using the emulsion-based manufacturing process of one or more embodiments of the present invention have utility in immediate release applications when administered to the respiratory tract. Rapid release is facilitated by: (a) the high specific surface area of the low density porous powders; (b) the small size of the drug crystals that are incorporated therein, and; (c) the low surface energy of the particles.

Alternatively, it may be desirable to engineer the particle matrix so that extended release of the active agent(s) is effected. This may be particularly desirable when the active agent(s) is rapidly cleared from the lungs or when sustained release is desired. For example, the nature of the phase behavior of phospholipid molecules is influenced by the nature of their chemical structure and/or preparation methods in spray-drying feedstock and drying conditions and other composition components utilized. In the case of spray-drying of active agent(s) solubilized within a small unilamellar vesicle (SUV) or multilamellar vesicle (MLV), the active agent(s) are encapsulated within multiple bilayers and are released over an extended time.

In contrast, spray-drying of a feedstock comprised of emulsion droplets and dispersed or dissolved active agent(s) in accordance with the teachings herein leads to a phospholipid matrix with less long-range order, thereby facilitating rapid release. While not being bound to any particular theory, it is believed that this is due in part to the fact that the active agent(s) are never formally encapsulated in the phospholipid, and the fact that the phospholipid is initially present on the surface of the emulsion droplets as a monolayer (not a bilayer as in the case of liposomes). The spray-dried particles prepared by the emulsion-based manufacturing process of one or more embodiments of the present invention often have a high degree of disorder. Also, the spray-dried particles typically have low surface energies, where values as low as 20 mN/m have been observed for spray-dried DSPC particles (determined by inverse gas chromatography). Small angle X-ray scattering (SAXS) studies conducted with spray-dried phospholipid particles have also shown a high degree of disorder for the lipid, with scattering peaks smeared out, and length scales extending in some instances only beyond a few nearest neighbors.

It should be noted that a matrix having a high gel to liquid crystal phase transition temperature is not sufficient in itself to achieve sustained release of the active agent(s). Having sufficient order for the bilayer structures is also important for achieving sustained release. To facilitate rapid release, an emulsion-system of high porosity (high surface area), and minimal interaction between the drug substance and phospholipid may be used. The pharmaceutical composition formation process may also include the additions of other composition components (e.g., small polymers such as Pluronic F-68; carbohydrates, salts, hydrotropes) to break the bilayer structure are also contemplated.

To achieve a sustained release, incorporation of the phospholipid in bilayer form may be used, especially if the active agent is encapsulated therein. In this case increasing the $T_m$ of the phospholipid may provide benefit via incorporation of divalent counterions or cholesterol. As well, increasing the interaction between the phospholipid and drug substance via the formation of ion-pairs (negatively charged active+steayl-amine, positively charged active+phosphatidylglycerol) would tend to decrease the dissolution rate. If the active is amphiphilic, surfactant/surfactant interactions may also slow active dissolution.

The addition of divalent counterions (e.g., calcium or magnesium ions) to long-chain saturated phosphatidylcho-lines results in an interaction between the negatively charged phosphate portion of the zwitterionic headgroup and the positively charged metal ion. This results in a displacement of water of hydration and a condensation of the packing of the phospholipid lipid headgroup and acyl chains. Further, this results in an increase in the Tm of the phospholipid. The decrease in headgroup hydration can have profound effects on the spreading properties of spray-dried phospholipid particles on contact with water. A fully hydrated phosphatidylcholine molecule will diffuse very slowly to a dispersed crystal via molecular diffusion through the water phase. The process is exceedingly slow because the solubility of the phospholipid in water is very low (about $10^{-10}$ mol/L for DPPC). Prior art attempts to overcome this phenomenon include homogenizing the crystals in the presence of the phospholipid. In this case, the high degree of shear and radius of curvature of the homogenized crystals facilitates coating of the phospholipid on the crystals. In contrast, "dry" phospholipid powders according to one or more embodiments of this invention can spread rapidly when contacted with an aqueous phase, thereby coating dispersed crystals without the need to apply high energies.

For example, upon reconstitution, the surface tension of spray-dried DSPC/Ca mixtures at the air/water interface decreases to equilibrium values (about 20 mN/m) as fast as a measurement can be taken. In contrast, liposomes of DSPC decrease the surface tension (about 50 mN/m) very little over a period of hours, and it is likely that this reduction is due to the presence of hydrolysis degradation products such as free fatty acids in the phospholipid. Single-tailed fatty acids can diffuse much more rapidly to the air/water interface than can the hydrophobic parent compound. Hence, the addition of calcium ions to phosphatidylcholines can facilitate the rapid encapsulation of crystalline drugs more rapidly and with lower applied energy.

In another version, the pharmaceutical composition comprises low density particles achieved by co-spray-drying nanocrystals with a perfluorocarbon-in-water emulsion. The nanocrystals may be formed by precipitation and may, e.g., range in size from about 45 μm to about 80 μm. Examples of perfluorocarbons include, but are not limited to, perfluorohexane, perfluorooctyl bromide, perfluorooctyl ethane, perfluorodecalin, perfluorobutyl ethane.

In accordance with the teachings herein the particles may be provided in a "dry" state. That is, in one or more embodiments, the particles will possess a moisture content that allows the powder to remain chemically and physically stable during storage at ambient or reduced temperature and remain dispersible. In this regard, there is little or no change in primary particle size, content, purity, and aerodynamic particle size distribution.

As such, the moisture content of the particles is typically less than about 10 wt %, such as less than about 6 wt %, less than about 3 wt %, or less than about 1 wt %. The moisture content is, at least in part, dictated by the composition and is controlled by the process conditions employed, e.g., inlet temperature, feed concentration, pump rate, and blowing agent type, concentration and post drying. Reduction in bound water leads to significant improvements in the dispersibility and flowability of phospholipid based powders, leading to the potential for highly efficient delivery of powdered lung surfactants or particle composition comprising active agent dispersed in the phospholipid. The improved dispersibility allows simple passive DPI devices to be used to effectively deliver these powders.

Yet another version of the pharmaceutical composition includes particle compositions that may comprise, or may be partially or completely coated with, charged species that prolong residence time at the point of contact or enhance penetration through mucosae. For example, anionic charges are known to favor mucoadhesion while cationic charges may be used to associate the formed particle with negatively charged bioactive agents such as genetic material. The charges may be imparted through the association or incorporation of polyanionic or polycationic materials such as polyacrylic acids, polylysine, polylactic acid, and chitosan.

In some versions, the pharmaceutical composition comprises particles having a mass median diameter less than about 20 µm, such as less than about 10 µm, less than about 7 µm, or less than about 5 µm. The particles may have a mass median aerodynamic diameter ranging from about 1 µm to about 6 µm, such as about 1.5 µm to about 5 µm, or about 2 µm to about 4 µm. If the particles are too large, a larger percentage of the particles may not reach the lungs. If the particles are too small, a larger percentage of the particles may be exhaled.

Unit doses of the pharmaceutical compositions may be contained in a container. Examples of containers include, but are not limited to, syringes, capsules, blow fill seal, blisters, vials, ampoules, or container closure systems made of metal, polymer (e.g., plastic, elastomer), glass, or the like. For instance, the vial may be a colorless Type I borosilicate glass ISO 6R 10 mL vial with a chlorobutyl rubber siliconized stopper, and rip-off type aluminum cap with colored plastic cover.

The container may be inserted into an aerosolization device. The container may be of a suitable shape, size, and material to contain the pharmaceutical composition and to provide the pharmaceutical composition in a usable condition. For example, the capsule or blister may comprise a wall which comprises a material that does not adversely react with the pharmaceutical composition. In addition, the wall may comprise a material that allows the capsule to be opened to allow the pharmaceutical composition to be aerosolized. In one version, the wall comprises one or more of gelatin, hydroxypropyl methylcellulose (HPMC), polyethyleneglycol-compounded HPMC, hydroxyproplycellulose, agar, aluminum foil, or the like. In one version, the capsule may comprise telescopically adjoining sections, as described for example in U.S. Pat. No. 4,247,066 which is incorporated herein by reference in its entirety. The size of the capsule may be selected to adequately contain the dose of the pharmaceutical composition. The sizes generally range from size 5 to size 000 with the outer diameters ranging from about 4.91 mm to 9.97 mm, the heights ranging from about 11.10 mm to about 26.14 mm, and the volumes ranging from about 0.13 mL to about 1.37 mL, respectively. Suitable capsules are available commercially from, for example, Shionogi Qualicaps Co. in Nara, Japan and Capsugel in Greenwood, S.C. After filling, a top portion may be placed over the bottom portion to form a capsule shape and to contain the powder within the capsule, as described in U.S. Pat. Nos. 4,846,876 and 6,357,490, and in WO 00/07572, which are incorporated herein by reference in their entireties. After the top portion is placed over the bottom portion, the capsule can optionally be banded.

For solutions, the amount of the composition in the unit dose typically ranges from about 2 ml to about 15 ml, such as from about 3 ml to about 10 ml, about 4 ml to about 8 ml, or about 5 ml to about 6 ml.

The compositions of the present invention may be made by any of the various methods and techniques known and available to those skilled in the art.

For instance, a solution of antiarrhythmic pharmaceutical agent may be made using the following procedure. Typically, manufacturing equipment is sterilized before use. A portion of the final volume, e.g., 70%, of solvent, e.g., water for injection, may be added into a suitable container. Antiarrhythmic pharmaceutical agent may then be added. The antiarrhythmic pharmaceutical agent may be mixed until dissolved. Additional solvent may be added to make up the final batch volume. The batch may be filtered, e.g., through a 0.2 μm filter into a sterilized receiving vessel. Filling components may be sterilized before use in filling the batch into vials, e.g., 10 ml vials.

As an example, the above-noted sterilizing may include the following. A 5 liter type 1 glass bottle and lid may be placed in an autoclave bag and sterilized at elevated temperature, e.g., 121° C. for 15 minutes, using an autoclave. Similarly, vials may be placed into suitable racks, inserted into an autoclave bag, and sterilized at elevated temperature, e.g., 121° C. for 15 minutes, using an autoclave. Also similarly, stoppers may be placed in an autoclave bag and sterilized at elevated temperature, e.g., 121° C. for 15 minutes, using an autoclave. Before sterilization, sterilizing filters may be attached to tubing, e.g., a 2 mm length of 7 mm×13 mm silicone tubing. A filling line may be prepared by placed in an autoclave bag and sterilized at elevated temperature, e.g., 121° C. for 15 minutes, using an autoclave.

The above-noted filtration may involve filtration into a laminar flow work area. The receiving bottle and filters may be set up in the laminar flow work area.

The above-noted filling may also be conducted under laminar flow protection. The filling line may be unwrapped and placed into the receiving bottle. The sterilized vials and stoppers may be unwrapped under laminar flow protection. Each vial may be filled, e.g., to a target fill of 5 g, and stoppered. A flip off collar may be applied to each vial. The sealed vials may be inspected for vial leakage, correct overseals, and cracks.

As another example, an antiarrhythmic may be prepared by lyophilizing the antiarrhythmic to form a powder for storage. The powder is then reconstituted prior to use. This technique may be used when the antiarrhythmic is unstable in solution.

The solvent for the solution to be lyophilized may comprise water. The solution may be excipient-free. For instance, the solution may be cryoprotectant-free.

In one or more embodiments, a suitable amount (e.g., 120 g per liter of final solution) of drug substance may be dissolved, e.g., in about the 75% of the theoretical total amount of water for injection under nitrogen bubbling. The dissolution time may be recorded and appearance may be evaluated.

Then, the dilution to the final volume with WFI may be carried out. Final volume may be checked. Density, pH, endotoxin, bioburden, and content by UV may be measured both before and after sterile filtration.

The solution may be filtered before lyophilizing. For instance, a double 0.22 μm filtration may be performed before filling. The filters may be tested for integrity and bubble point before and after the filtration.

Pre-washed and autoclaved vials may be aseptically filled using an automatic filling line to a target of 5 ml per vial and then partially stoppered. In process check for fill volumes may be done by checking the fill weight every 15 minutes.

The lyophilizing is generally conducted within about 72 hours, such as within about 8 hours, or within about 4 hours, of the dissolving.

In one or more embodiments, the lyophilizing comprises freezing the solution to form a frozen solution. The frozen solution is typically held at an initial temperature ranging from about −40° C. to about −50° C., such as about −45° C.

During the initial temperature period, the pressure around the frozen solution is typically atmospheric pressure. The initial temperature period typically ranges from about 1 hour to about 4 hours, such about 1.5 hours to about 3 hours, or about 2 hours.

The lyophilizing may further comprise raising a temperature of the frozen solution to a first predetermined temperature, which may range from about 10° C. to about 20° C., such as about 15° C. The time for the heat ramp from the initial temperature to the first predetermined temperature generally ranges from about 6 hours to about 10 hours, such as about 7 hours to about 9 hours.

During the first predetermined temperature period, the pressure around the solution typically ranges from about 100 μbar to about 250 μbar, such as about 150 μbar to about 225 μbar. The solution may be held at the first predetermined temperature for a period ranging from about 20 hours to about 30 hours, such as from about 24 hours.

The lyophilizing may still further comprise raising a temperature of the solution to a second predetermined temperature, which may range from about 25° C. to about 35° C., such as about 30° C. During the second predetermined temperature period, the pressure around the frozen solution typically ranges from about 100 μbar to about 250 μbar, such as about 150 μbar to about 225 μbar. The solution may be held at the second predetermined temperature for a period ranging from about 10 hours to about 20 hours.

In view of the above, the lyophilization cycle may comprise a freezing ramp, e.g., from 20° C. to −45° C. in 65 minutes, followed by a freeze soak, e.g., at −45° C. for 2 hours. Primary drying may be accomplished with a heating ramp, e.g., from −45° C. to 15° C. in 8 hours, followed by a temperature hold, e.g., at 15° C. for 24 hours at a pressure of 200 μbar. Secondary drying may be accomplished with a heating ramp, e.g., from 15° C. to 30° C. in 15 minutes, followed by a temperature hold at 30° C. for 15 hours at a pressure of 200 μbar. At the end of the lyophilization cycle, the vacuum may be broken with sterile nitrogen, and the vials may be automatically stoppered.

The water content of the lyophilized powder is typically less than about 7 wt %, such as less than about 5 wt %, less than about 4 wt %, less than about 3 wt %, less than about 2 wt %, or less than about 1 wt %.

The powder is capable of being reconstituted with water at 25° C. and 1.0 atmosphere and with manual agitation, in less than about 60 seconds, such as less than about 30 seconds, less than about 15 seconds, or less than about 10 seconds.

The powder typically has a large specific surface area that facilitates reconstitution. The specific surface area typically ranges from about 5 $m^2/g$ to about 20 $m^2/g$, such as about 8 $m^2/g$ to 15 $m^2/g$, or about 10 $m^2/g$ to 12 $m^2/g$.

Upon reconstitution with water, the antiarrhythmic pharmaceutical agent solution typically has a pH that ranges from about 2.5 to about 7, such as about 3 to about 6.

For dry powders, the composition may be formed by spray drying, lyophilization, milling (e.g., wet milling, dry milling), and the like.

In spray drying, the preparation to be spray dried or feedstock can be any solution, coarse suspension, slurry, colloidal dispersion, or paste that may be atomized using the selected spray drying apparatus. In the case of insoluble agents, the feedstock may comprise a suspension as described above. Alternatively, a dilute solution and/or one or more solvents may be utilized in the feedstock. In one or more embodiments, the feed stock will comprise a colloidal system such as an emulsion, reverse emulsion microemulsion, multiple emulsion, particle dispersion, or slurry.

In one version, the antiarrhythmic pharmaceutical agent and the matrix material are added to an aqueous feedstock to form a feedstock solution, suspension, or emulsion. The feedstock is then spray dried to produce dried particles comprising the matrix material and the antiarrhythmic pharmaceutical agent. Suitable spray-drying processes are known in the art, for example as disclosed in WO 99/16419 and U.S. Pat. Nos. 6,077,543; 6,051,256; 6,001,336; 5,985,248; and 5,976,574, which are incorporated herein by reference in their entireties.

Whatever components are selected, the first step in particle production typically comprises feedstock preparation. If a phospholipids-based particle is intended to act as a carrier for the antiarrhythmic pharmaceutical agent, the selected active agent(s) may be introduced into a liquid, such as water, to produce a concentrated suspension. The concentration of antiarrhythmic pharmaceutical agent and optional active agents typically depends on the amount of agent required in the final powder and the performance of the delivery device employed (e.g., the fine particle dose for a metered dose inhaler (MDI) or a dry powder inhaler (DPI)).

Any additional active agent(s) may be incorporated in a single feedstock preparation and spray dried to provide a single pharmaceutical composition species comprising a plurality of active agents. Conversely, individual active agents could be added to separate stocks and spray dried separately to provide a plurality of pharmaceutical composition species with different compositions. These individual species could be added to the suspension medium or dry powder dispensing compartment in any desired proportion and placed in the aerosol delivery system as described below.

Polyvalent cation may be combined with the antiarrhythmic pharmaceutical agent suspension, combined with the phospholipid emulsion, or combined with an oil-in-water emulsion formed in a separate vessel. The antiarrhythmic pharmaceutical agent may also be dispersed directly in the emulsion.

For example, polyvalent cation and phospholipid may be homogenized in hot distilled water (e.g., 70° C.) using a suitable high shear mechanical mixer (e.g., Ultra-Turrax model T-25 mixer) at 8000 rpm for 2 to 5 min. Typically, 5 to 25 g of fluorocarbon is added dropwise to the dispersed surfactant solution while mixing. The resulting polyvalent cation-containing perfluorocarbon in water emulsion may then be processed using a high pressure homogenizer to reduce the particle size. Typically, the emulsion is processed for five discrete passes at 12,000 to 18,000 PSI and kept at about 50° C. to about 80° C.

When the polyvalent cation is combined with an oil-in-water emulsion, the dispersion stability and dispersibility of the spray dried pharmaceutical composition can be improved by using a blowing agent, as described in WO 99/16419, which is incorporated herein by reference in its entirety. This process forms an emulsion, optionally stabilized by an incorporated surfactant, typically comprising submicron droplets of water immiscible blowing agent dispersed in an aqueous continuous phase. The blowing agent may be a fluorinated compound (e.g., perfluorohexane, perfluorooctyl bromide, perfluorooctyl ethane, perfluorodecalin, perfluorobutyl ethane) which vaporizes during the spray-drying process, leaving behind generally hollow, porous aerodynamically light particles. Other suitable liquid blowing agents include non-fluorinated oils, chloroform, Freon® fluorocarbons, ethyl acetate, alcohols, hydrocarbons, nitrogen, and carbon dioxide gases. The blowing agent may be emulsified with a phospholipid.

Although the pharmaceutical compositions may be formed using a blowing agent as described above, it will be appreciated that, in some instances, no additional blowing agent is required and an aqueous dispersion of the antiarrhythmic pharmaceutical agent and/or pharmaceutically acceptable excipients and surfactant(s) are spray dried directly. In such cases, the pharmaceutical composition may possess certain physicochemical properties (e.g., high crystallinity, elevated melting temperature, surface activity, etc.) that make it particularly suitable for use in such techniques.

As needed, cosurfactants such as poloxamer 188 or span 80 may be dispersed into this annex solution. Additionally, pharmaceutically acceptable excipients such as sugars and starches can also be added.

The feedstock(s) may then be fed into a spray dryer. Typically, the feedstock is sprayed into a current of warm filtered air that evaporates the solvent and conveys the dried product to a collector. The spent air is then exhausted with the solvent. Commercial spray dryers manufactured by Buchi Ltd. or Niro Corp. may be modified for use to produce the pharmaceutical composition. Examples of spray drying methods and systems suitable for making the dry powders of one or more embodiments of the present invention are disclosed in U.S. Pat. Nos. 6,077,543; 6,051,256; 6,001,336; 5,985,248; and 5,976,574, which are incorporated herein by reference in their entireties.

Operating conditions of the spray dryer such as inlet and outlet temperature, feed rate, atomization pressure, flow rate of the drying air, and nozzle configuration can be adjusted in order to produce the required particle size, and production yield of the resulting dry particles. The selection of appropriate apparatus and processing conditions are within the purview of a skilled artisan in view of the teachings herein and may be accomplished without undue experimentation. Exemplary settings are as follows: an air inlet temperature between about 60° C. and about 170° C.; an air outlet between about 40° C. to about 120° C.; a feed rate between about 3 mL/min to about 15 mL/min; an aspiration air flow of about 300 L/min; and an atomization air flow rate between about 25/min and about 50 L/min. The settings will, of course, vary depending on the type of equipment used. In any event, the use of these and similar methods allow formation of aerodynamically light particles with diameters appropriate for aerosol deposition into the lung.

Hollow and/or porous microstructures may be formed by spray drying, as disclosed in WO 99/16419, which is incorporated herein by reference. The spray-drying process can result in the formation of a pharmaceutical composition comprising particles having a relatively thin porous wall defining a large internal void. The spray-drying process is also often advantageous over other processes in that the particles formed are less likely to rupture during processing or during deagglomeration.

Pharmaceutical compositions useful in one or more embodiments of the present invention may alternatively be formed by lyophilization. Lyophilization is a freeze-drying process in which water is sublimed from the composition after it is frozen. The lyophilization process is often used because biologics and pharmaceuticals that are relatively unstable in an aqueous solution may be dried without exposure to elevated temperatures, and then stored in a dry state where there are fewer stability problems. With respect to one or more embodiments of the instant invention, such techniques are particularly compatible with the incorporation of peptides, proteins, genetic material and other natural and synthetic macromolecules in pharmaceutical compositions without compromising physiological activity. Lyophilized cake containing a fine foam-like structure can be micronized using techniques known in the art to provide particles of the desired size.

The compositions of one or more embodiments of the present invention may be administered by inhalation.

Moreover, the doses of composition that are inhaled are typically much less than those administered by other routes and required to obtain similar effects, due to the efficient targeting of the inhaled composition to the heart.

In one or more embodiments of the invention, a pharmaceutical composition comprising antiarrhythmic pharmaceutical agent is administered to the lungs of a patient in need thereof. For example, the patient may have been diagnosed with an arrhythmia. Examples of arrhythmias include, but are not limited to, tachycardia, supraventricular tachycardia (SVT), paroxysmal supraventricular tachycardia (PSVT), atrial fibrillation (AF), paroxysmal atrial fibrillation (PAF), permanent atrial fibrillation, persistent atrial fibrillation, atrial flutter, paroxysmal atrial flutter, and lone atrial fibrillation.

Thus, the pharmaceutical compositions of one or more embodiments of the present invention can be used to treat and/or provide prophylaxis for a broad range of patients. A suitable patient for, receiving treatment and/or prophylaxis as described herein is any mammalian patient in need thereof, preferably such mammal is a human. Examples of patients include, but are not limited to, pediatric patients, adult patients, and geriatric patients. In some embodiments, the composition is intended only as a treatment for rapid resolution of symptoms and is not taken as a preventative, i.e., when the patient is well, there is no need for drug—this makes the therapy more effective and safe due to sporadic or intermittent dosing, and focused on reducing disabling symptoms.

The dosage necessary and the frequency of dosing of the antiarrhythmic pharmaceutical agent depend on the composition and concentration of the antiarrhythmic pharmaceutical agent within the composition. In some cases, the dose is less than its normal intravenous dose. The pulmonary dose is similar to intracardial doses. Inhalation avoids dilution of drug in the body as compared to intravenous or oral dosing.

Inhalation also avoids metabolism, such as hepatic metabolism. For instance, calcium channel blockers, such as diltiazem, undergo significant hepatic metabolism when taken orally. Inhalation allows rapid delivery of the parent diltiazem compound to the heart as a bolus. Surprisingly, administration by inhalation of diltiazem via the inhalation route according to the present invention converted atrial fibrillation to normal sinus rhythm and reduced heart rate. Thus, administration by inhalation of diltiazem is useful for treating both atrial fibrillation and supraventricular tachycardia (SVT). In contrast, administration by IV of diltiazem is typically only used for converting SVT to normal sinus rhythm and in atrial fibrillation to reduce heart rate (not for converting to normal sinus rhythm).

Inhalation also avoids red blood cell metabolism. For instance, the reduced dilution and short route associated with inhalation reduces red blood cell metabolism of esmolol.

Inhalation may also avoid reduced blood pressure and fainting. For instance, IV administration of beta blockers, such as esmolol, may reduce mean arterial blood pressure (MAP). Inhalation allows rapid delivery of esmolol without reducing MAP. As a result, inhalation of beta blockers may result in an MAP of 10 mm Hg to 20 mm Hg greater than the MAP resulting from IV administration of the same beta blocker.

With inhaled cardiotherapy the drug is directed to the heart from the lungs as a bolus. So, the heart sees a high concentration. The drug is rapidly diluted as it passes through the heart, but the exposure time is sufficient for the desired pharmacological action. Once the drug passes through the heart, the concentration of the drug in the overall blood is below the therapeutic concentration and is considered ineffective. The therapeutic window is the range of dosage of a drug or of its concentration in a bodily system that provides safe effective therapy. Anything below the minimum amount is sub-therapeutic and hence ineffective in that concentration. In view of the dilution, unwanted side effects are minimized.

In one version, the antiarrhythmic may be administered daily. In this version, the daily dosage of antiarrhythmic pharmaceutical agent ranges from about 0.1 mg to about 600 mg, such as about 0.5 mg to about 500 mg, about 1 mg to about 400 mg, about 2 mg to about 300 mg, and about 3 mg to about 200 mg.

The dose may be administered during a single inhalation or may be administered during several inhalations. The fluctuations of antiarrhythmic pharmaceutical agent concentration can be reduced by administering the pharmaceutical composition more often or may be increased by administering the pharmaceutical composition less often. Therefore, the pharmaceutical composition of one or more embodiments of the present invention may be administered from about four times daily to about once a month, such as about once daily to about once every two weeks, about once every two days to about once a week, and about once per week.

For treating a patient suffering from an arrhythmia, the amount per dose of antiarrhythmic pharmaceutical agent administered may be an amount that is effective to treat the arrhythmia. The amount of antiarrhythmic pharmaceutical agent for the treatment of arrhythmia will generally be higher than that used for prevention, and will typically range from about 0.001 mg/kg to 6 mg/kg, such as from about 0.002 mg/kg to about 5 mg/kg, or from about 0.005 mg/kg to about 4 mg/kg. In one exemplary treatment regimen, the formulation in accordance with one or more embodiments of the invention may be administered about 1 to about 4 times daily, such as from about 2 to about 3 times daily. Generally, the dose of antiarrhythmic pharmaceutical agent delivered to a patient will range from about 0.1 mg to about 600 mg, such as from about 0.2 mg to 500 mg daily, depending on the condition being treated, the age and weight of the patient, and the like.

For instance, the present invention may involve a follow-up inhalation if no cardioversion occurs after an initial inhalation. Typically, if no cardioversion occurs within 30 minutes of the initial inhalation, the follow-up dosage is higher or the same as the initial dosage.

The dosing may be guided by how the patient feels. Also or alternatively, dosing may be guided by a portable ECG. For instance, the dosing may be guided by a Holter monitor.

In another version, the pharmaceutical composition is administered prophylactically to a patient who is likely to develop an arrhythmia. For example, a patient who has a history of arrhythmias can be prophylactically treated with a pharmaceutical composition comprising antiarrhythmic pharmaceutical agent to reduce the likelihood of developing an arrhythmia.

The pharmaceutical composition may be administered to a patient in any regimen which is effective to prevent an arrhythmia. Illustrative prophylactic regimes include administering an antiarrhythmic pharmaceutical agent as described herein 1 to 21 times per week.

While not wishing to be bound by theory, by providing the antiarrhythmic pharmaceutical agent in accordance with one or more embodiments of the invention, the systemic exposure of the antiarrhythmic pharmaceutical agent can be reduced by avoiding initial dilution. As noted above, the antiarrhythmic pharmaceutical agent undergoes dilution as and after it passes through the heart. Thus, the administration via inhalation of antiarrhythmic pharmaceutical agent is believed to be safer than intravenous delivery.

In another aspect, a method of administering comprises administering to free breathing patients by way of an aerosol generator device and/or system for administration of aerosolized medicaments such as those disclosed in U.S. Published Application Nos. 20050235987, 20050211253, 20050211245, 20040035413, and 20040011358, the disclosures of which are incorporated herein by reference in their entireties.

In one version, the pharmaceutical composition may be delivered to the lungs of a patient in the form of a dry powder. Accordingly, the pharmaceutical composition comprises a dry powder that may be effectively delivered to the deep lungs or to another target site. This pharmaceutical composition is in the form of a dry powder comprising particles having a size selected to permit penetration into the alveoli of the lungs.

In some instances, it is desirable to deliver a unit dose, such as doses of 0.1 mg or 100 mg or greater of an antiarrhythmic pharmaceutical agent to the lung in a single inhalation. The above described phospholipid hollow and/or porous dry powder particles allow for doses of about 5 mg or greater, often greater than about 10 mg, and sometimes greater than about 15 mg, to be delivered in a single inhalation and in an advantageous manner. Alternatively, a dosage may be delivered over two or more inhalations, such as 1 to 6, 1 to 5, or 1 to 4, inhalations. For example, a 10 mg dosage may be delivered by providing two unit doses of 5 mg each, and the two unit doses may be separately inhaled. In certain embodiments, the overall dose of the antiarrhythmic pharmaceutical agent ranges from 0.1 mg to 200 mg, such as 0.5 mg to 150 mg, or 1 mg to 100 mg.

The time for dosing is typically short. For nebulizers the dosing time usually ranges from 1 minute to 20 minutes, such as from 2 minutes to 15 minutes, or from 3 minutes to 10 minutes. Regarding dry powders, for a single capsule, the total dosing time is normally less than about 1 minute. Thus, the time for dosing may be less than about 5 min, such as less than about 4 min, less than about 3 min, less than about 2 min, or less than about 1 min.

In certain embodiments, the present invention is directed to a method of self-diagnosing and treating atrial arrhythmia. The method comprises self-diagnosing atrial arrhythmia by detecting at least one of shortness of breath, heart palpitations, and above normal heart rate. The method also comprises self-administering by inhalation an effective amount of at least one antiarrhythmic pharmaceutical agent within two hours, such as within one hour, 30 minutes, or within 15 minutes, of the self-diagnosing.

In certain embodiments, the patient can self-titrate. For example, the patient can self-administer, e.g., by using a nebulizer, until disabling symptoms disappear. In some cases, the self-administering continues until the patient no longer feels heart palpitations.

The time for onset of action is also typically short. For instance, the patient may have normal sinus rhythm within 20 minutes of initiating the administering, such as within 15 minutes, within 10 minutes, or within 5 minutes of initiating the administering. The rapid onset of action is advantageous because the longer a patient has had arrhythmia, the longer it typically takes to convert the patient to normal sinus rhythm.

In some embodiments, the method of the present invention allows the patient to avoid other therapies, such as ablation and/or electrical cardioversion. In other embodiments, the method of the present invention is used in combination with other therapies, such as before or after electrical cardioversion and/or ablation therapy.

The dispersions or powder pharmaceutical compositions may be administered using an aerosolization device. The aerosolization device may be a nebulizer, a metered dose inhaler, a liquid dose instillation device, or a dry powder inhaler. The pharmaceutical composition may be delivered by a nebulizer as described in WO 99/16420, by a metered dose inhaler as described in WO 99/16422, by a liquid dose instillation apparatus as described in WO 99/16421, and by a dry powder inhaler as described in U.S. Published Application Nos. 20020017295 and 20040105820, WO 99/16419, WO 02/83220, and U.S. Pat. No. 6,546,929, which are incorporated herein by reference in their entireties. As such, an inhaler may comprise a canister containing the particles or particles and propellant, and wherein the inhaler comprises a metering valve in communication with an interior of the canister. The propellant may be a hydrofluoroalkane.

The formulations of the present invention may be administered with nebulizers, such as that disclosed in PCT WO 99/16420, the disclosure of which is hereby incorporated in its entirety by reference, in order to provide an aerosolized medicament that may be administered to the pulmonary air passages of a patient in need thereof. Nebulizers are known in the art and could easily be employed for administration of the claimed formulations without undue experimentation. Breath activated nebulizers, as well as those comprising other types of improvements which have been, or will be, developed are also compatible with the formulations of the present invention and are contemplated as being with in the scope thereof.

Nebulizers impart energy into a liquid pharmaceutical formulation to aerosolize the liquid, and to allow delivery to the pulmonary system, e.g., the lungs, of a patient. A nebulizer comprises a liquid delivery system, such as a container having a reservoir that contains a liquid pharmaceutical formulation. The liquid pharmaceutical formulation generally comprises an active agent that is either in solution or suspended within a liquid medium.

In one type of nebulizer, generally referred to as a jet nebulizer, compressed gas is forced through an orifice in the container. The compressed gas forces liquid to be withdrawn through a nozzle, and the withdrawn liquid mixes with the flowing gas to form aerosol droplets. A cloud of droplets is then administered to the patients respiratory tract.

In another type of nebulizer, generally referred to as a vibrating mesh nebulizer, energy, such as mechanical energy, vibrates a mesh. This vibration of the mesh aerosolizes the liquid pharmaceutical formulation to create an aerosol cloud that is administered to the patient's lungs.

Alternatively or additionally, the pharmaceutical formulation may be in a liquid form and may be aerosolized using a nebulizer as described in WO 2004/071368, which is herein incorporated by reference in its entirety, as well as U.S. Published application Nos. 2004/0011358 and 2004/0035413, which are both herein incorporated by reference in their entireties. Other examples of nebulizers include, but are not limited to, the Aeroneb®Go or Aeroneb®Pro nebulizers, available from Aerogen Ltd. of Galway, Ireland; the PARI eFlow and other PARI nebulizers available from PARI Respiratory Equipment, Inc. of Midlothian, Va.; the Lumiscope® Nebulizer 6600 or 6610 available from Lumiscope Company, Inc. of East Brunswick, N.J.; and the Omron NE-U22 available from Omron Healthcare, Inc. of Kyoto, Japan.

It has been found that a nebulizer of the vibrating mesh type, such as one that that forms droplets without the use of compressed gas, such as the Aeroneb® Pro provides unexpected improvement in dosing efficiency and consistency. By generating fine droplets by using a vibrating perforated or unperforated membrane, rather than by introducing compressed air, the aerosolized pharmaceutical formulation can be introduced without substantially affecting the flow characteristics. In addition, the generated droplets when using a nebulizer of this type are introduced at a low velocity, thereby decreasing the likelihood of the droplets being driven to an undesired region.

In still another type of nebulizer, ultrasonic waves are generated to directly vibrate and aerosolize the pharmaceutical formulation.

As noted above, the present invention may also involve a dry powder inhaler. A specific version of a dry powder aerosolization apparatus is described in U.S. Pat. Nos. 4,069,819 and 4,995,385, which are incorporated herein by reference in their entireties. Another useful device, which has a chamber that is sized and shaped to receive a capsule so that the capsule is orthogonal to the inhalation direction, is described in U.S. Pat. No. 3,991,761, which is incorporated herein by reference in its entirety. As also described in U.S. Pat. No. 3,991,761, a puncturing mechanism may puncture both ends of the capsule. In another version, a chamber may receive a capsule in a manner where air flows through the capsule as described for example in U.S. Pat. Nos. 4,338,931 and 5,619,985, which are incorporated herein by reference in their entireties. In another version, the aerosolization of the pharmaceutical composition may be accomplished by pressurized gas flowing through the inlets, as described for example in U.S. Pat. Nos. 5,458,135; 5,785,049; and 6,257,233, or propellant, as described in WO 00/72904 and U.S. Pat. No. 4,114,615, which are incorporated herein by reference. These types of dry powder inhalers are generally referred to as active dry powder inhalers.

Other dry powder inhalers include those available from Boehringer Ingelheim (e.g., Respimat inhaler), Hovione (e.g., FlowCaps inhaler), Plastiape (e.g., Osmohaler inhaler), and MicroDose. The present invention may also utilize condensation aerosol devices, available from Alexza, Mountain View, Calif. Yet another useful inhaler is disclosed in WO 2008/051621, which is incorporated herein by reference in its entirety.

The pharmaceutical formulations disclosed herein may also be administered to the lungs of a patient via aerosolization, such as with a metered dose inhaler. The use of such formulations provides for superior dose reproducibility and improved lung deposition as disclosed in WO 99/16422, hereby incorporated in its entirety by reference. MDIs are known in the art and could easily be employed for administration of the claimed dispersions without undue experimentation. Breath activated MDIs and pressurized MDIs (pMDIs), as well as those comprising other types of improvements which have been, or will be, developed are also compatible with the formulations of the present invention and, as such, are contemplated as being within the scope thereof.

Along with DPIs, MDIs and nebulizers, it will be appreciated that the formulations of one or more embodiments of the present invention may be used in conjunction with liquid dose instillation or LDI techniques as disclosed in, for example, WO 99/16421, which is incorporated herein by reference in its entirety. Liquid dose instillation involves the direct administration of a formulation to the lung. With respect to LDI the formulations are preferably used in conjunction with partial liquid ventilation or total liquid ventilation. Moreover, one or more embodiments of the present invention may further comprise introducing a therapeutically beneficial amount of a physiologically acceptable gas (such as nitric oxide or oxygen) into the pharmaceutical microdispersion prior to, during or following administration.

The pharmaceutical composition of one or more embodiments of the present invention typically has improved emitted dose efficiency. Accordingly, high doses of the pharmaceutical composition may be delivered using a variety of aerosolization devices and techniques.

Figure 7:
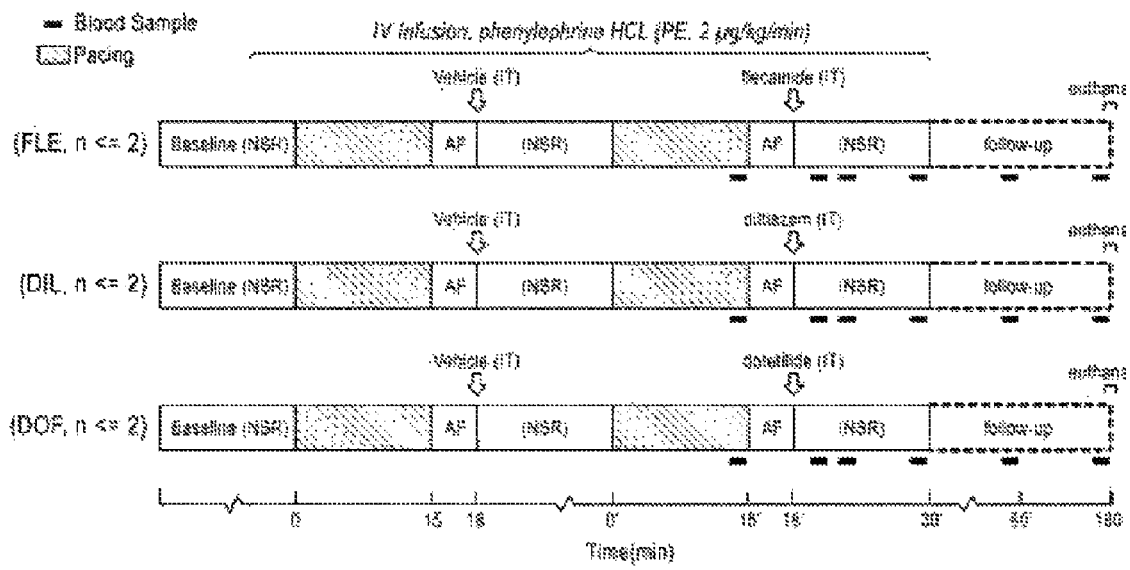
FIG. 7 shows a representative study outline: effects of flecainide (FLE, n=2), diltiazem (DIL, n=2), and dofetilide (DOF, n=2) on induced atrial-fibrillation. NSR: normal sinus rhythm.

The emitted dose (ED) of the particles of the present invention may be greater than about 30%, such as greater than about 40%, greater than about 50%, greater than about 60%, or greater than about 70%.

One or more embodiments are directed to kits. For instance, the kit may include an aerosolization device and a container, e.g., unit dose receptacle, containing aerosolizable antiarrhythmic pharmaceutical agent, e.g., liquid or dry powder.

The kit may further comprise a package, such as a bag, that contains the aerosolization device and the container.

In view of the above, the present invention involves methods to treat acute episodes of and/or chronic arrhythmias. In certain embodiments, the treating comprises acute treatment after detection of atrial arrhythmia.

This method of treatment results in a pulsatile pharmacokinetic profile and transient pharmacodynamic effect mimicking the effect of an IV. This method delivers high drug concentrations that are safe and effective to the heart, while the distribution to the rest of the body results in the drug being diluted to sub-therapeutic levels. This method is the shortest route of delivery to the heart next to intra-cardial injection. This provides the convenience of self-administration like the "pill-in-the-pocket" approach, but the effectiveness and fast onset of action of an IV. Although the delivery of medications through the lung for systemic effect is not new, it was thought it wouldn't be effective to the heart, because of the fast passage of drug through it. The PK/PD modeling originating this invention shows that the drug exposure is sufficient for therapeutic effect at a much lower dose compared to other routes of administration. This method ensures dug concentrations in overall plasma are much lower than what is achieved by oral/IV hence minimizing drug-drug interactions and side effects.

The present invention will be further illustrated by way of the following Examples. These examples are non-limiting and do not restrict the scope of the invention. Unless stated otherwise, all percentages, parts, etc. presented in the examples are by weight.

EXAMPLES

Example 1

Prophetic Analytical Model Involving Verapamil and Lidocaine

Published pharmacokinetic and pharmacodynamic models (FIG. 4) show relationships between drug concentration in coronary blood and desired coronary effect. IV drug information was used from published literature. HARRISON et al., "Effect of Single Doses of Inhaled Lignocaine on FEV1 and Bronchial Reactivity in Asthma," Respir Med., 12:1359-635 (December 1992). Inhaled drug information was simulated based on known properties of pulmonary small molecule absorption.

FIG. 5 shows the different time concentration profiles of drug administered via the IV and inhalation routes. Verapamil was selected as an example heart drug as it possesses both cardiac rate and rhythm control properties and is often used to rescue acute arrhythmia episodes (e.g.: paroxysmal ventricular tachycardia and paroxysmal atrial fibrillation).

FIG. 6 also shows different time concentration profiles of drug administered via the IV and inhalation routes. Lidocaine was selected as an example heart drug. This PK/PD modeling with lidocaine shows same high feasibility.

Example 2

Effects of Intratracheal (IT) Administration of Anti-Arrhythmic Compounds on the Ventricular Response of Dogs with Induced Atrial Fibrillation and Supraventricular Tachycardia (SVT)

Objective:

To evaluate the effects/efficacy of common antiarrhythmic drugs when given via the pulmonary route, on the electrophysiological response of anesthetized dogs with induced atrial fibrillation and supraventricular tachycardia.

Animal Models Used

Atrial Fibrillation Model:

Anesthesia/Surgical Preparation:

A venous catheter was placed in a peripheral vessel (i.e., cephalic) for administration of anesthetic. For anesthesia induction, all animals were given morphine sulfate (~2 mg/kg) and a bolus of alpha chloralose (~100 mg/kg) intravenously through the venous catheter. Anesthesia was sustained with alpha chloralose (35-75 mg/kg/hour IV), until completion of the study (<2 hours). Following induction, animals were endotracheally intubated and mechanically ventilated (~12 breaths/minute with a tidal volume of 200-300 mL). Subsequently, a cut-down on a jugular vein permitted introduction of a pacing lead into the right atrium. Transthoracic electrodes forming ECG lead II were placed. For test/vehicle article delivery, a 4F catheter was introduced through the trachea and wedged into a small airway, and a venous catheter was placed in a peripheral vessel (i.e., cephalic).

Experiments:

Following instrumentation and hemodynamic stabilization (for at least 15 minutes), phenylephrine was continuously infused (2 ug/kg/min IV) to elevate the systemic arterial pressure and increase vagal (parasympathetic) efferent activity for the duration of the study. Approximately 5 min after administration of this parasympathomimetic was started; the following experiments were performed:

First, the right atrium was paced (20 V, 40 Hz, 4 ms pulse) for 15 minutes, and following pacing discontinuation, atrial fibrillation ensued. Approximately 3 minutes after pacing was stopped and atrial fibrillation was observed, the animals were given vehicle (~3 mL) intra-tracheally (IT); the duration between dosing and, (if observed) the return to sinus rhythm and/or the ventricular rate was noted. Observations were made for up to 10 minutes.

Subsequently, atrial fibrillation was re-established via 15-minute pacing cycle(s), as described above. Once pacing was discontinued and atrial fibrillation was observed/stable for 3 minutes, the animals were administered the vehicle or one of the test articles, delivered as a bolus (~3 mL) directly into a small airway through the intratracheal catheter. Vehicle was only water. In the case of flecainide as the test article, the concentration was 15 mg of flecainide/3 ml of water. Following dosing, the duration between cessation of administration and, if observed, return to sinus rhythm and/or ventricular rate were noted; observations were made for up to 10 minutes. Overall, three groups/test-articles were studied, and up to two animals were assigned to each group (n=2/group): one group received flecainide acetate (2-4 mg/kg, FLE), while the others received diltiazem (0.25-0.50 mg/kg, DIL) or dofetilide (20-60 ug/kg, DOF); only one test article was administered per animal. The experimental protocol(s) are summarized in FIG. 7.

Supraventricular Tachycardia Model:
Anesthesia/Surgical Preparation:

A venous catheter was placed in a peripheral vessel (i.e., cephalic) for administration of anesthetic(s). For anesthesia induction, all animals were given a combination of diazepam (~0.5 mg/kg) and ketamine (~10 mg/kg) intravenously through this venous catheter. Anesthesia was sustained until completion of the study with an intravenous infusion of pentobarbital (5-15 mg/kg/hr). Following induction, animals were endotracheally intubated and mechanically ventilated (~12 breaths/min with a tidal volume of 200-300 mL).

Subsequently, a cut-down on a jugular vein permitted the introduction of a pacing lead into the right atrium. Similarly, for arterial pressure monitoring, a solid-state micromanometer catheter (Millar Instruments) was advanced into the aortic root via a cut-down over an artery (e.g., femoral, carotid). Transthoracic electrodes forming ECG lead II was placed. For vehicle/test article delivery, a 4F catheter was introduced through the trachea and wedged into a small airway, and a venous catheter was placed in a peripheral vessel (i.e., cephalic).

Experiments:

Following instrumentation/hemodynamic stabilization (for at least 15 minutes), right atrial pacing (5-10 V, 40 Hz, 2 ms pulses) was established in order to induce supraventricular tachycardia (SVT); pacing and SVT was sustained throughout the duration of the experiments. Approximately 5 minutes after onset of SVT and while monitoring ECG/arterial pressure continuously, the animals were administered three escalating doses (one at a time) of a test article; each dose was delivered as a bolus (~3 mL) directly into a small airway through the intratracheal catheter (IT). Following dosing, the heart-rate (HR) and arterial pressure response were monitored for 15 minutes.

Subsequently (once the response to three IT doses had been recorded), hemodynamic recovery was allowed for approximately 30 minutes, and the electrocardiographic/hemodynamic response to the highest test-article dose was re-evaluated; however, for comparison purposes, this dose was delivered intravenously (IV).

Figure 8:
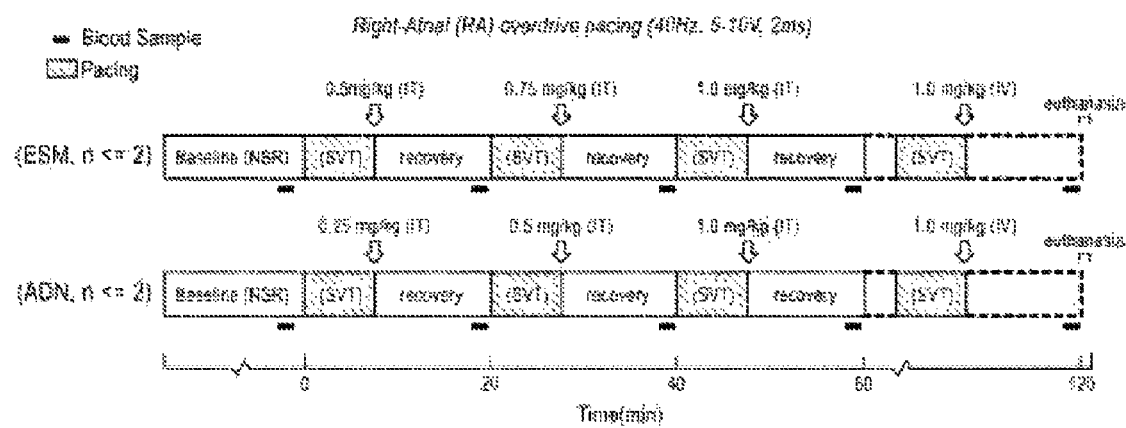
FIG. 8 shows a representative study outline: dose-response of intratracheal (IT) esmolol HCL (ESM, n<=2) or adenosine (ADN, n<=2) on induced supra-ventricular tachycardia (SVT). NSR: normal sinus rhythm. IV: intravenous

Overall, two groups/test-articles were studied, and up to two animals were assigned to each group (n=2/group): one group received esmolol HCL (0.5-1.0 mg/kg, ESM), while the other received adenosine (0.25-1.0 mg/kg, ADN); only one test article was administered to per animal. The experimental protocol(s) are summarized in FIG. 8.

Observations:
Atrial Fibrillation:

Among the three test articles (flecainide, diltiazem and dofetilide) studied, both flecainide and diltiazem rapidly converted the Atrial Fibrillation to normal sinus rhythm, while dofetilide marginally slowed the ventricular rate.

Figure 9:
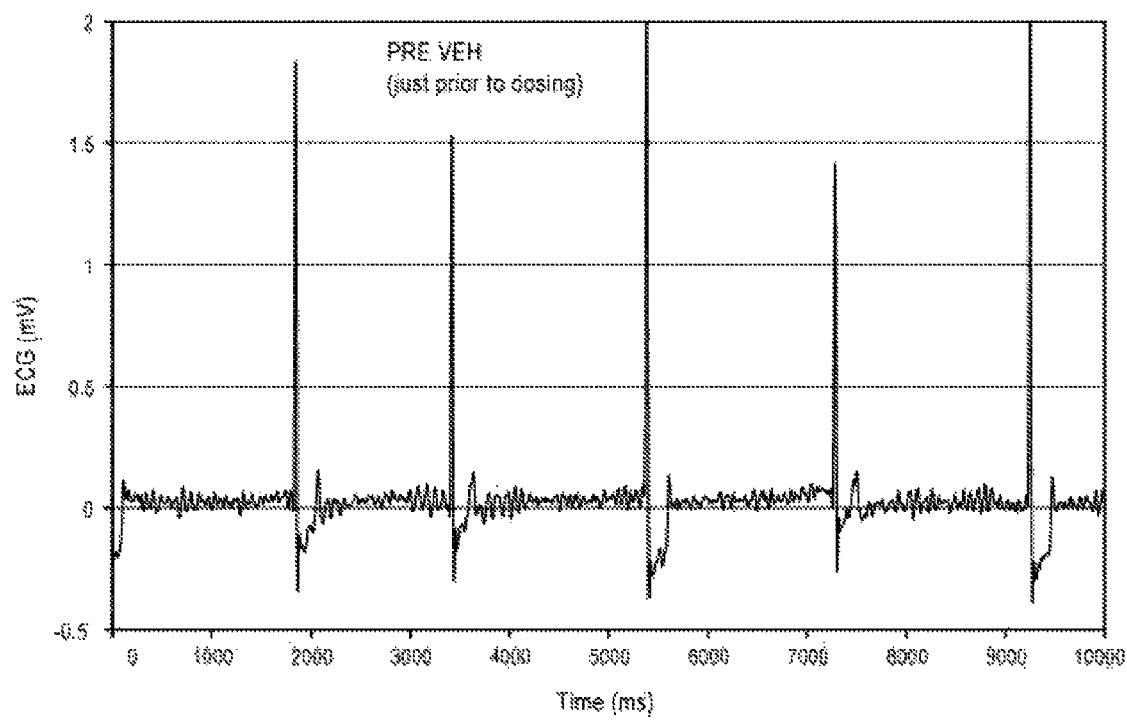
FIG. 9 shows an ECG trace showing Dog in Afib prior to dosing of either vehicle or test article.
Figure 10:
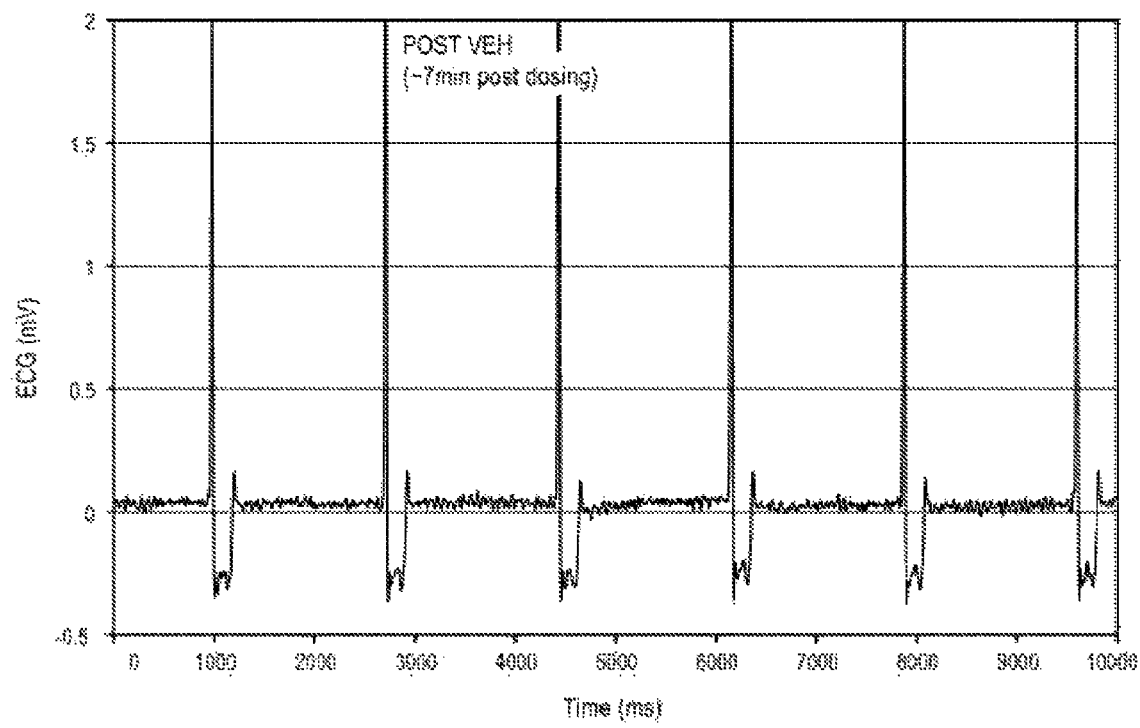
FIG. 10 shows an ECG trace showing Dog continues to be in Afib after pulmonary administration of vehicle (water, 3 ml).

Vehicle:

FIG. 9 shows the dog in atrial fibrillation prior to administration of either vehicle or test article. FIG. 10 shows an example of the vehicle having no effect on the arrhythmia. Vehicle administered in same volumes as the test articles had no effect on the arrhythmia.

Figure 11:
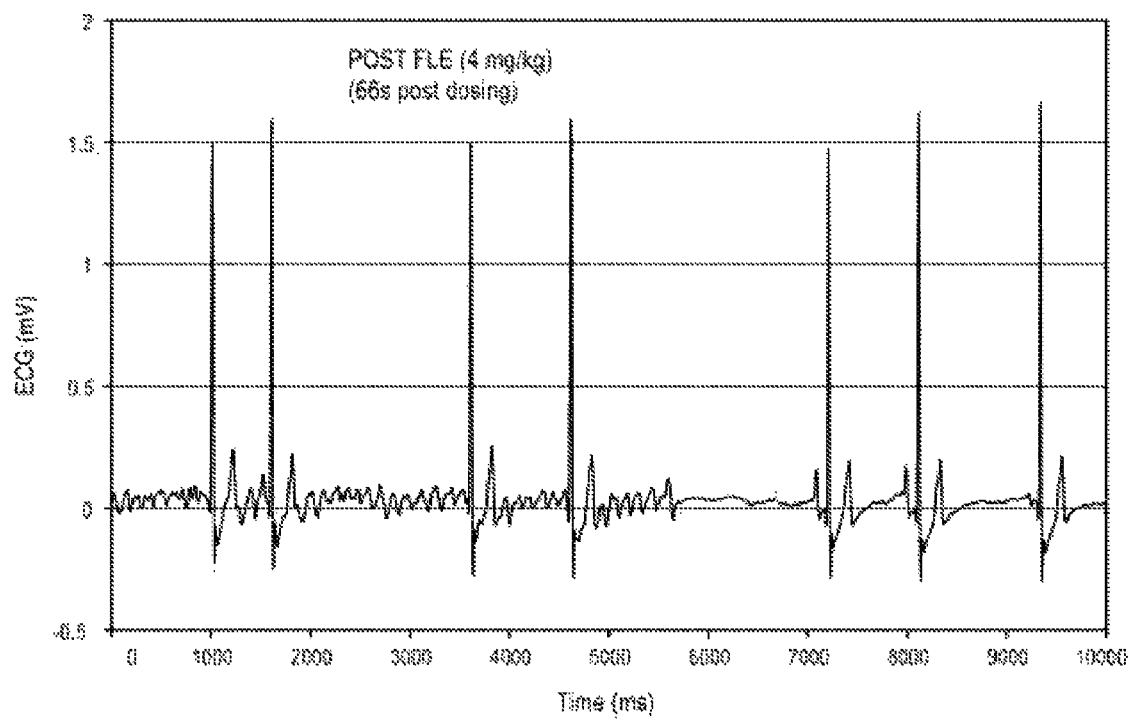
FIG. 11 shows an ECG trace showing the Afib converting into normal sinus rhythm when a dog was administered 4 mg/kg body weight of Flecainide acetate.
Figure 12:
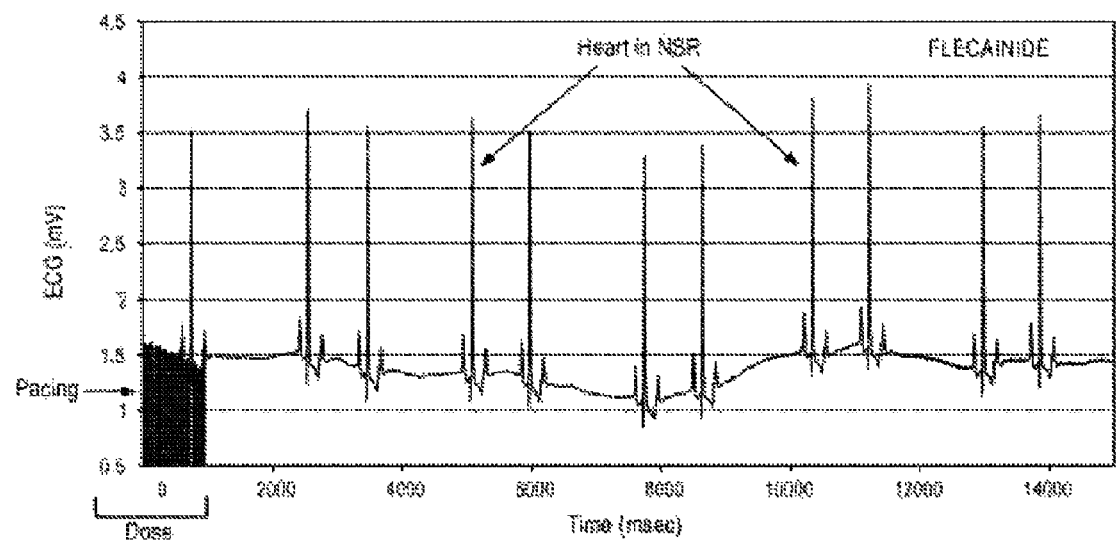
FIG. 12 shows an ECG trace showing Afib converting as soon as dosing occurred at 2 mg/kg body weight of flecainide acetate.

Flecainide:

At pulmonary dose between 2-4 mg/kg body weight, flecainide converted the induced atrial fibrillation to normal sinus rhythm. Large doses of the drug also resulted in slower ventricular rates. None to minimal drop in mean arterial pressure was noted. Neither dogs exhibited any known adverse events such as proarrhythmia. See FIGS. 11 and 12.

Figure 13:
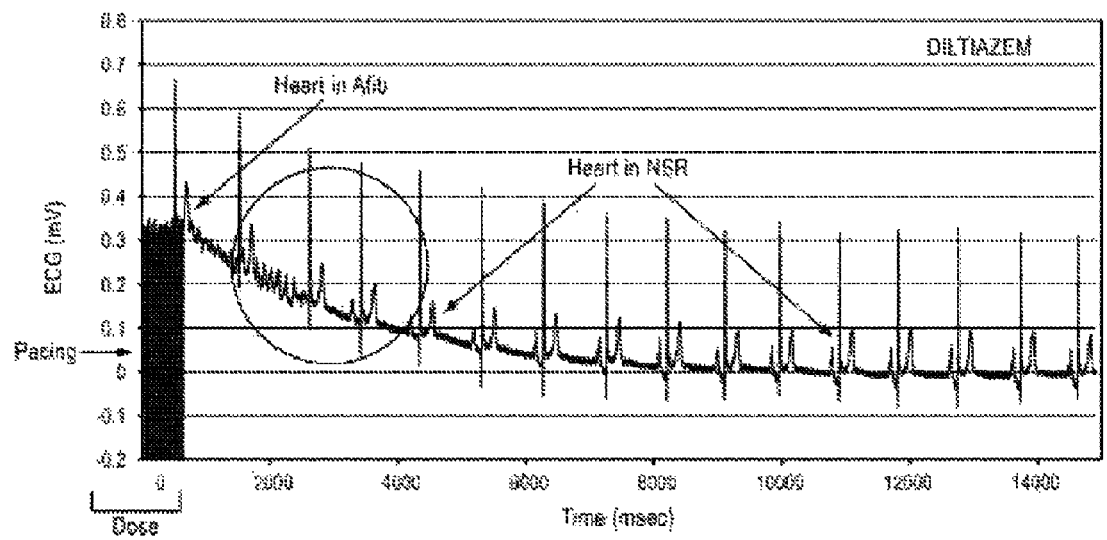
FIG. 13 shows an ECG trace showing Afib converting after administration of diltiazem HCl at 0.25 mg/kg body weight.

Diltiazem:

At pulmonary doses of 0.25 mg/kg body weight, diltiazem converted the induced atrial fibrillation to normal sinus rhythm and also prolonged the PQ. Heart rate also slowed down marginally. There was however a notable drop in mean arterial blood pressure (MAP). See FIG. 13.

Dofetilide:

At escalating pulmonary doses of 10-40 mcg/kg body weight, dofetilide caused minor reduction in heart rate.

Figure 14:
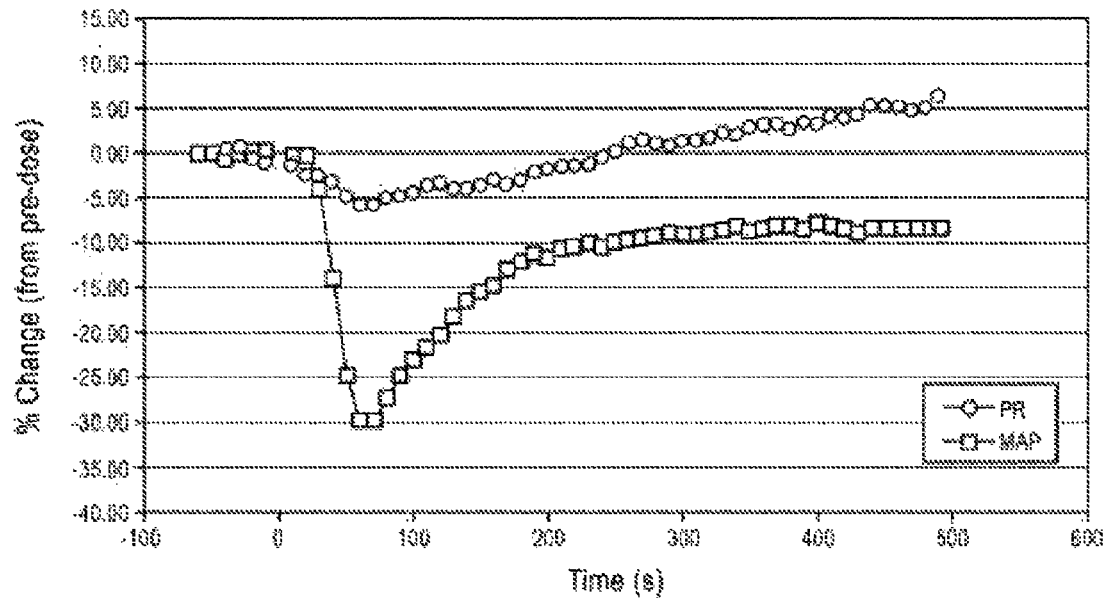
FIG. 14 shows results from a supraventricular tachycardia model in which PR interval and Mean Arterial blood pressure (MAP) change in time after pulmonary administration of pulmonary diltiazem 0.25 mg/kg.
Figure 15:
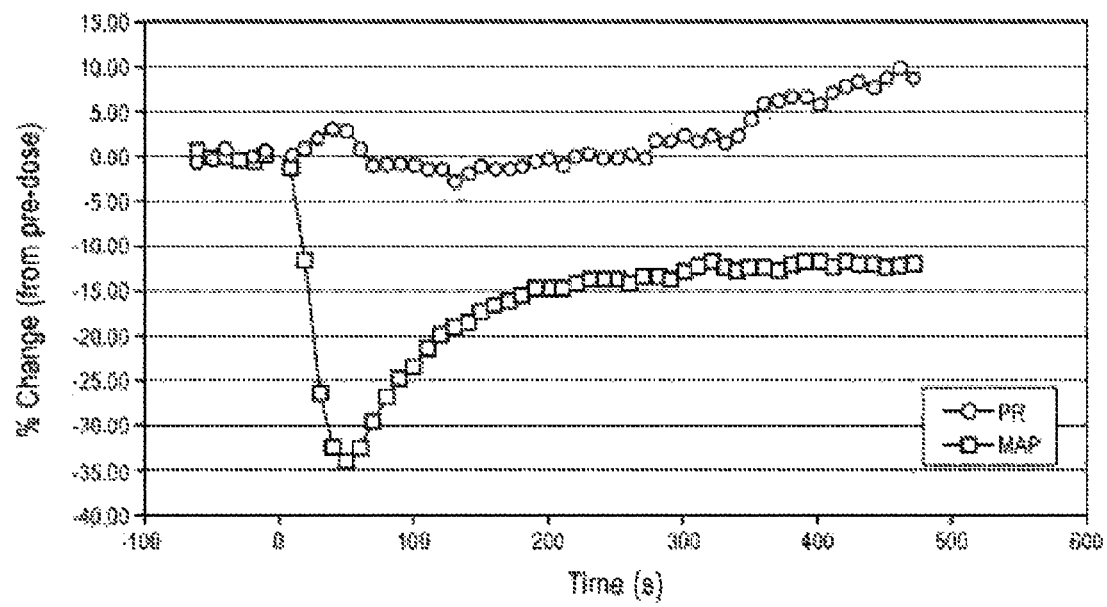
FIG. 15 shows results from the supraventricular tachycardia model in which PR interval and Mean Arterial blood pressure (MAP) change in time after intravenous administration of pulmonary diltiazem 0.25 mg/kg.
Figure 16:
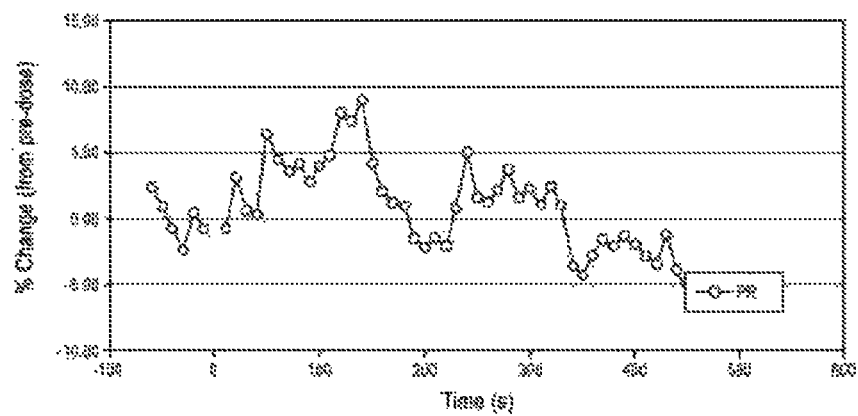
FIG. 16 shows results from the supraventricular tachycardia model showing effect on PR interval over time of 0.5 mg/kg body weight of esmolol HCl administered via the lung (IT).
Figure 17:
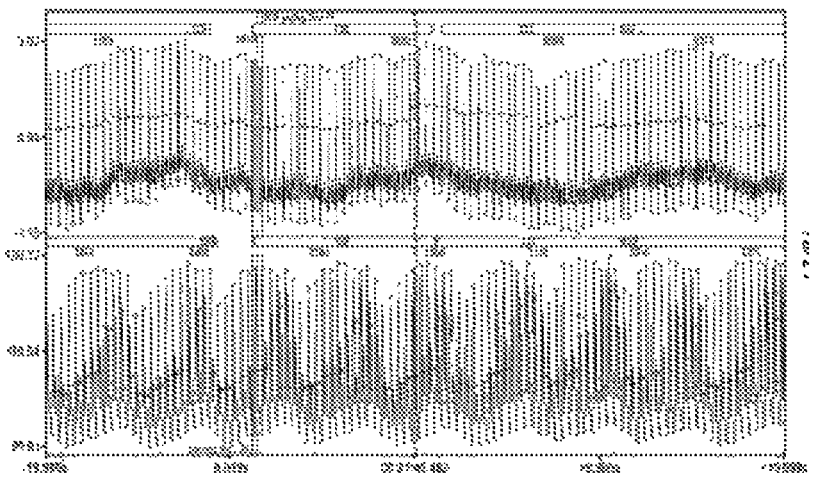
FIG. 17 shows results from the supraventricular tachycardia model showing period of AV block induced by esmolol 0.5 mg/kg administered via the lung.
Figure 18:
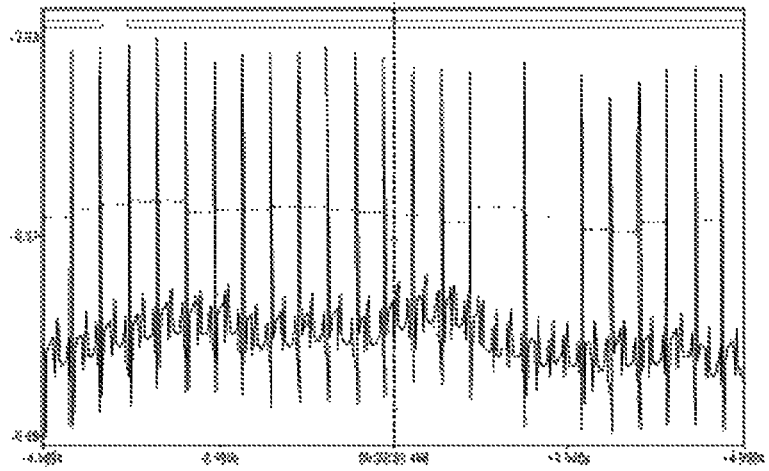
FIG. 18 shows results from the supraventricular tachycardia model showing period of AV block induced by esmolol 0.5 mg/kg administered via the lung.
Figure 19:
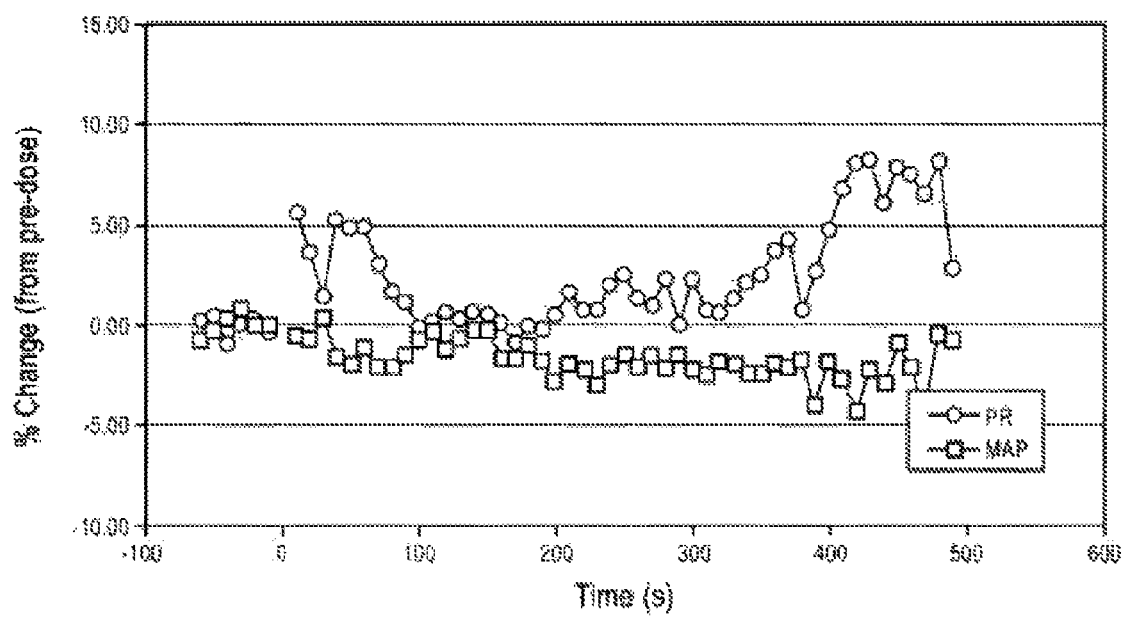
FIG. 19 shows results from the supraventricular tachycardia model showing effect on PR interval over time of 0.5 mg/kg body weight of esmolol HCl administered via the lung (IT).
Figure 20:
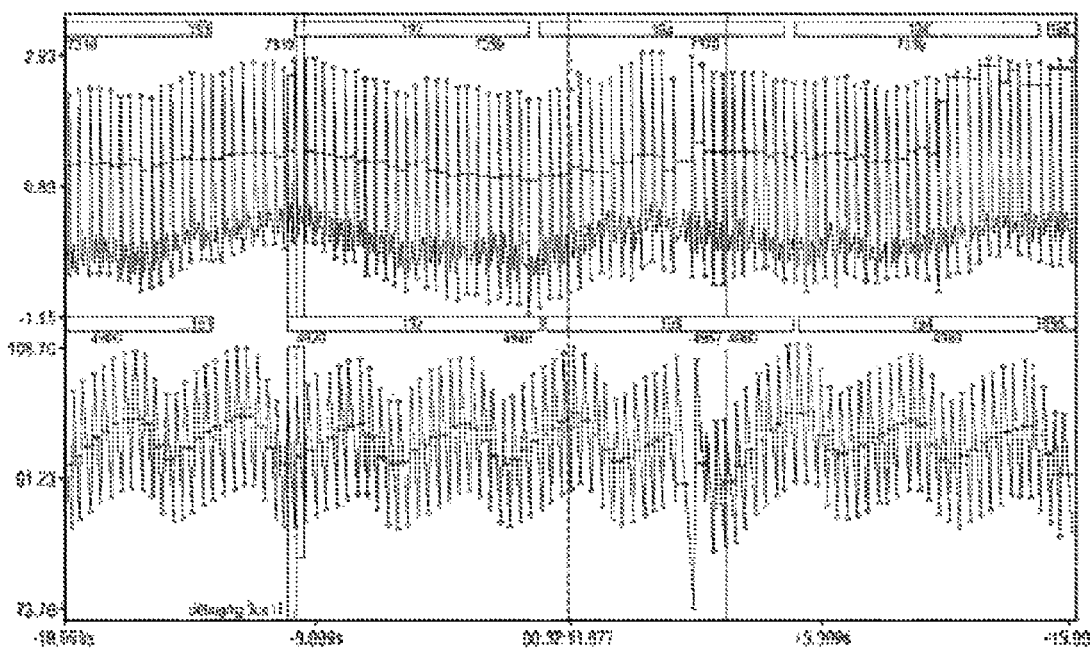
FIG. 20 shows results from the supraventricular tachycardia model showing period of AV block induced by esmolol 0.75 mg/kg administered via the lung.

Supraventricular Tachycardia (SVT):
Diltiazem:

The diltiazem delivered via the pulmonary and IV routes were comparable in all aspects. The Mean Arterial Pressure (MAP) dropped significantly in both cases, attributed directly to the dose of the drug. Diltiazem also prolonged the PR interval indicating that the drug delivered by either IV or pulmonary routes has the ability to correct the SVT to normal sinus rhythm. The timing of the electrophysiological change was comparable between IV and pulmonary. See FIGS. 14 and 15.

Esmolol:

Elevating doses of esmolol were shown to produce $2^{nd}$ degree AV block at lower doses and also affecting the PR intervals in the ECG traces. See FIGS. 16-20.

However, higher doses of esmolol at 1.0 mg/kg did not produce the same electrophysiological effects. It is noteworthy that esmolol delivered via the lung did not cause a drop in MAP in any of the doses.

Adenosine:

Adenosine administered via the lung did not have any effect on the heart. Adenosine is known to metabolize differently in different species and it is not clear whether the effect was due to localized adenosine administration or the model not being sensitive enough.

Summary

There was a clear cardiovascular effect of diltiazem, flecainide, and a probable effect of esmolol and dofetilide when given intratracheally. These drugs comprise four divergent classes of chemical and pharmacological agents. Although a clear response was not observed with adenosine, it is still considered worthy of evaluation in more specific animal models. The responses mimicked qualtitatively those of the IV route and known physiological effects of all test articles for diltiazem, flecainide, and esmolol. There may be some physical or physicochemical property of adenosine that precludes absorption from the tracheal route in this animal model. Additionally, administration into a single small airway would not be expected to produce the same exposure as administration by inhalation where the surface for diffusion would be many orders of magnitude greater.

These studies confirm the physiological effects of divergent chemicals on cardiovascular function. The intratracheal route of administration possesses 3 potential advantages. (1) It is the shortest route from point of administration to the target organ—the heart. (2) There is less dilution therefore a higher concentration to the target organ would be expected. (3) There would be a reduction in metabolism (i.e., first pass effect) since there is no organ (e.g., liver) for metabolizing between site of administration and target organ.

Example 3

Preliminary Evaluation of Solubility and Taste of Antiarrhythmic Pharmaceutical Agents when Administered as an Aerosol Objective:

To evaluate the solubilities of flecainide acetate and diltiazem hydrochloride in water and to evaluate the acceptability of taste and aftertaste of these two drugs for administration as liquid aerosols.

Experiment and Observations:

Preformulation Studies:

Diltiazem's solubility was >90 mg/mL at room temperature. The pH of a 3.5 mg/mL solution of diltiazem in water was 6.7. At 50 mg/mL, a diltiazem in water solution was about 80% to isotonic.

Flecainide's solubility was about 30 mg/mL at room temperature. The pH of a 2.6 mg/mL solution of flecainide in water was 5.0. At 30 mg/mL, a flecainide in water solution was about 50% to isotonic.

The following solution strengths were prepared for taste evaluation: (1) diltiazem hydrochloride—50 mg/ml solution in distilled water; and (2) flecainide acetate—30 mg/ml solution in distilled water. The solutions were clear with no visible particulate matter.

Inhalation Device:

The Aeroneb®GO device was used because it is a simple-to-use device developed specifically for patients who require respiratory therapy in and away from the home. The device can be used by patients of all ages (infant through adult) and aerosolizes solutions intended for inhalation. Aeroneb® Go works with either an AC wall controller or a battery pack, and can be cleaned with soap and water. More details about this device can be obtained at www.aerogen.com.

Inhalation Procedure:

Volunteers:

Number of subjects: 2 healthy male volunteers

Volunteer-1: age—48

Volunteer-2: age—63

Nebulizer Testing:

Water was poured into the nebulizer cup, and the nebulizer was turned on. The visible cloud of aerosol generated when the nebulizer was turned on was treated as a qualitative aerosol standard.

Flecainide Acetate:

About 1 ml of the 30 mg/ml solution was poured into the cup of the nebulizer. The nebulizer was turned on and the resulting aerosol was similar to but not as dense as the aerosol formed with the water alone.

The nebulizer was then placed in the mouth and switched on. Deep lung inhalation was performed through the nebulizer. About 40 μl (~1.2 mg of flecainide acetate) of the test solution was inhaled. The inhaled dose was sub-therapeutic in nature as it was much less than the regular 100 mg administered as tablets. Flecainide acetate is also available as an IV injection in Europe as 10 mg/ml strength in 15 ml ampoules.

Diltiazem Hydrochloride:

About 1 ml of the 50 mg/ml solution was poured into the cup of the nebulizer. The nebulizer was turned on and the resulting aerosol was similar to but not as dense as the aerosol formed with the water alone.

The nebulizer was then placed in the mouth and a switched on. Deep lung inhalation was performed through the nebulizer. About 40 μl (~2 mg of diltiazem hydrochloride) of the test solution was inhaled. The inhaled dose was sub-therapeutic in nature as it was much less than the IV injection marketed in the U.S. as 5 mg/ml in 5 ml vials.

CONCLUSIONS AND OBSERVATIONS

1. The visible aerosol characteristics test solutions were similar to each other but not as dense as the water.
2. Flecainide acetate: The taste feedback from both volunteers was very similar.
   a. Taste: Mildly bitter taste felt in the back of the tongue
   b. Aftertaste: There was none to little aftertaste 5 minutes after the inhalation maneuver.
3. Diltiazem hydrochloride: Water was inhaled to wash out any of the flecainide residues. The taste feedback from both volunteers was very similar.
   a. Taste: Mildly bitter taste felt in the back of the tongue
   b. Aftertaste: There was none to little aftertaste 5 minutes after the inhalation maneuver.
4. Other observations:
   a. No burning sensations was felt in the mouth, throat, or lungs
   b. No visible adverse events were observed. Both volunteers rested for 60 minutes after dosing.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art.

Having now fully described this invention, it will be understood to those of ordinary skill in the art that the methods of the present invention can be carried out with a wide and equivalent range of conditions, formulations, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of treating atrial arrhythmia, comprising:
   administering to a pulmonary vein through a pulmonary tract and through use of an aerosolization device an effective amount of at least one antiarrhythmic pharmaceutical agent selected from a group consisting of class I, class II, class III, and class IV antiarrhythmics, to a patient in need thereof,
   wherein the effective amount of the at least one antiarrhythmic pharmaceutical agent is a total amount from 0.1 mg to 200 mg administered over multiple inhalations,
   wherein the aerosolization device is a nebulizer configured to administer the at least one antiarrhythmic pharmaceutical agent in a liquid pharmaceutical formulation, wherein aerosolization occurs at room temperature,
   wherein the at least one antiarrhythmic pharmaceutical agent level peaks in a coronary sinus of a heart of the patient at a time between 30 seconds and 20 minutes from initiation of the administering to the pulmonary vein, wherein the patient's sinus rhythm is restored to normal within 30 minutes of initiation of the administering to the pulmonary vein, wherein 1) a concentration of the at least one antiarrhythmic pharmaceutical agent in the coronary sinus of the heart is between 0.1 mg/L and 60 mg/L at 2.5 minutes after initiation of the administering to the pulmonary vein, and the concentration is less than 0.1 mg/L at 30 minutes after initiation of the administering to the pulmonary vein; or 2) 10% to 60% of a nominal dose of the at least one antiarrhythmic pharmaceutical agent reaches the coronary sinus, and wherein the method does not comprise administering an adenosine derivative.

2. The method of claim 1, wherein the concentration of the at least one antiarrhythmic pharmaceutical agent in the coronary sinus of the heart is between 0.1 mg/L and 20 mg/L at 2.5 minutes after initiation of the administering to the pulmonary vein, and the concentration is less than 0.1 mg/L at 30 minutes after initiation of the administering to the pulmonary vein.

3. The method of claim 1, wherein the administering to the pulmonary vein comprises up to 6 inhalations.

4. The method of claim 1, wherein the atrial arrhythmia comprises tachycardia.

5. The method of claim 4, wherein the tachycardia is selected from the group consisting of: supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter, and lone atrial fibrillation.

6. The method of claim 1, comprising administering nebulized droplets comprising the at least one antiarrhythmic pharmaceutical agent, wherein the nebulized droplets have a mass median aerodynamic diameter of less than 10 µm.

7. The method of claim 1, wherein the antiarrhythmic pharmaceutical agent is a class I antiarrhythmic.

8. The method of claim 7, wherein the class I antiarrhythmic is a class Ia, Ib, or Ic antiarrhythmic.

9. The method of claim 1, wherein the antiarrhythmic pharmaceutical agent is a class II antiarrhythmic.

10. The method of claim 9, wherein the class II antiarrhythmic is esmolol HCl.

11. The method of claim 10, wherein dosage of the esmolol HCl is between 0.5 and 0.75 mg/kg body weight.

12. The method of claim 1, wherein the antiarrhythmic pharmaceutical agent is a class IV antiarrhythmic.

13. The method of claim 12, wherein the class IV antiarrhythmic is diltiazem.

14. The method of claim 13, wherein dosage of the diltiazem is 0.25 to 0.50 mg/kg body weight.

15. The method of claim 1, wherein the at least one antiarrhythmic pharmaceutical agent level peaks in the coronary sinus of the heart at a time between 1 minute and 10 minutes.

16. The method of claim 1, wherein the at least one antiarrhythmic pharmaceutical agent is self-administered by the patient.

17. A method of treating atrial arrhythmia, comprising:
administering to a pulmonary vein through a pulmonary tract and through use of an aerosolization device an effective amount of at least one antiarrhythmic pharmaceutical agent selected from a group consisting of class I, class II, class III, and class IV antiarrhythmics, to a patient in need thereof, wherein the patient self-administers and self-titrates an effective inhaled dose of the at least one antiarrhythmic pharmaceutical agent for a conversion of atrial arrhythmia to normal sinus rhythm, wherein the aerosolization device is a nebulizer configured to administer the at least one antiarrhythmic pharmaceutical agent in a liquid pharmaceutical formulation, wherein the aerosolization occurs at room temperature, wherein the at least one antiarrhythmic pharmaceutical agent level peaks in a coronary sinus of a heart of the patient at a time between 30 seconds and 20 minutes from initiation of the administering to the pulmonary vein, wherein the patient's sinus rhythm is restored to normal within 30 minutes of initiation of the administering to the pulmonary vein, wherein 1) a concentration of the at least one antiarrhythmic pharmaceutical agent in the coronary sinus of the heart is between 0.1 mg/L and 60 mg/L at 2.5 minutes after initiation of the administering the effective amount of the at least one antiarrhythmic pharmaceutical agent to the pulmonary vein, and the concentration is less than 0.1 mg/L at 30 minutes after initiation of the administering to the pulmonary vein; or 2) 10% to 60% of a nominal dose of the at least one antiarrhythmic pharmaceutical agent reaches the coronary sinus, and wherein the method does not comprise administering an adenosine derivative.

18. The method of claim 17, wherein the concentration of the at least one antiarrhythmic pharmaceutical agent in the coronary sinus of the heart is between 0.1 mg/L and 20 mg/L at 2.5 minutes after initiation of the administering to the pulmonary vein, and the concentration is less than 0.1 mg/L at 30 minutes after initiation of the administering to the pulmonary vein.

19. The method of claim 17, wherein the administering to the pulmonary vein comprises up to 6 inhalations.

20. The method of claim 1, wherein the atrial arrhythmia comprises tachycardia.

21. The method of claim 20, wherein the tachycardia is selected from the group consisting of: supraventricular tachycardia, paroxysmal supraventricular tachycardia, atrial fibrillation, paroxysmal atrial fibrillation, acute episodes in persistent and permanent atrial fibrillation, atrial flutter, paroxysmal atrial flutter, and lone atrial fibrillation.

22. The method of claim 1, comprising administering nebulized droplets comprising the at least one antiarrhythmic pharmaceutical agent, wherein the nebulized droplets have a mass median aerodynamic diameter of less than 10 µm.

23. The method of claim 1, wherein the antiarrhythmic pharmaceutical agent is a class I antiarrhythmic.

24. The method of claim 23, wherein the class I antiarrhythmic is a class Ia, Ib, or Ic antiarrhythmic.

25. The method of claim 1, wherein the antiarrhythmic pharmaceutical agent is a class II antiarrhythmic.

26. The method of claim 25, wherein the class II antiarrhythmic is esmolol HCl.

27. The method of claim 26, wherein the effective inhaled dose of the esmolol HCl is between 0.5 and 0.75 mg/kg body weight.

28. The method of claim 1, wherein the antiarrhythmic pharmaceutical agent is a class IV antiarrhythmic.

29. The method of claim 28, wherein the class IV antiarrhythmic is diltiazem.

30. The method of claim 29, wherein the effective inhaled dose of the diltiazem is 0.25 to 0.50 mg/kg body weight.

31. The method of claim 1, wherein the at least one antiarrhythmic pharmaceutical agent level peaks in the coronary sinus of the heart at a time between 1 minute and 10 minutes.

* * * * *